(12) United States Patent
Di Paola et al.

(10) Patent No.: US 10,894,114 B2
(45) Date of Patent: Jan. 19, 2021

(54) DRIVELINE BONE ANCHORS AND METHODS OF USE

(71) Applicant: TC1 LLC, St. Paul, MN (US)

(72) Inventors: John Mark Di Paola, Livermore, CA (US); Eric Lee, Oakland, CA (US); John Duc Nguyen, San Ramon, CA (US); Carine Hoarau, Pleasant Hill, CA (US); Yi-Ren Woo, Livermore, CA (US); Chris Eskildsen, Pleasant Hill, CA (US); Pete Cardamone, Brentwood, CA (US); John J. Hagerty, Jr., Livermore, CA (US)

( * ) Notice: Subject to any disclaimer, the term of this patent is extended or adjusted under 35 U.S.C. 154(b) by 67 days.

(21) Appl. No.: 15/870,119

(22) Filed: Jan. 12, 2018

(65) Prior Publication Data

US 2018/0200420 A1    Jul. 19, 2018

Related U.S. Application Data

(60) Provisional application No. 62/445,536, filed on Jan. 12, 2017.

(51) Int. Cl.
*A61M 1/00* (2006.01)
*A61M 1/10* (2006.01)
*A61M 1/12* (2006.01)

(52) U.S. Cl.
CPC ........ *A61M 1/1008* (2014.02); *A61M 1/1086* (2013.01); *A61M 1/122* (2014.02); *A61M 1/127* (2013.01); *A61M 1/1031* (2014.02)

(58) Field of Classification Search
USPC ......................................................... 600/16
See application file for complete search history.

(56) References Cited

U.S. PATENT DOCUMENTS 3,663,965 A    5/1972  Lee et al.
4,230,096 A   10/1980  Zeff et al.
(Continued)

FOREIGN PATENT DOCUMENTS

CN    1288757      3/2001
EP    1812094 B1   8/2011
(Continued)

OTHER PUBLICATIONS

Reichenbach et al., "Chronic Implantation of a Skeletal Muscle Energy Convertor for Cardiac Assist Devices", A Preliminary Report, ASAIO Journal,, 1998, 7 pages.
(Continued)

*Primary Examiner* — Nicole F Lavert
(74) *Attorney, Agent, or Firm* — Kilpatrick Townsend & Stockton LLP

(57) ABSTRACT

Systems, methods, and devices for securing a driveline to a bone are disclosed herein. The driveline can connect an external controller to an implantable blood pump. The bone anchor can include a driveline capture portion. The driveline capture portion can receive the driveline and fix a position of the driveline with respect to the driveline capture portion. The driveline capture portion includes: a driveline receiver that can receive the driveline; and a driveline anchor that can engage the driveline to fix the position of the driveline with respect to the driveline receiver. The bone anchor can include a bone capture portion. The bone capture portion can engage a bone and fix a position of the bone with respect to the bone capture portion.

14 Claims, 13 Drawing Sheets

(56) References Cited

U.S. PATENT DOCUMENTS

| | | | |
|---|---|---|---|
| 4,449,975 A | 5/1984 | Perry | |
| 4,925,443 A | 5/1990 | Heilman et al. | |
| 5,224,935 A | 7/1993 | Hollands | |
| 5,344,385 A | 9/1994 | Buck et al. | |
| 5,395,344 A | 3/1995 | Beisang | |
| 5,653,676 A | 8/1997 | Buck et al. | |
| 5,695,471 A | 12/1997 | Wampler | |
| 5,888,242 A | 3/1999 | Antaki et al. | |
| 5,904,646 A * | 5/1999 | Jarvik | A61M 39/0247 600/16 |
| 6,071,093 A | 6/2000 | Hart | |
| 6,116,862 A | 9/2000 | Rau et al. | |
| 6,186,665 B1 | 2/2001 | Maher et al. | |
| 6,234,772 B1 | 5/2001 | Wampler et al. | |
| 6,264,635 B1 | 7/2001 | Wampler et al. | |
| 6,572,587 B2 | 6/2003 | Lerman et al. | |
| 6,688,861 B2 | 2/2004 | Wampler | |
| 6,991,595 B2 | 1/2006 | Burke et al. | |
| 7,361,185 B2 | 4/2008 | Omalley et al. | |
| 7,686,829 B2 | 3/2010 | Elliott et al. | |
| 7,699,586 B2 | 4/2010 | LaRose et al. | |
| 7,927,352 B2 | 4/2011 | Wilke et al. | |
| 7,976,271 B2 | 7/2011 | LaRose et al. | |
| 7,997,854 B2 | 8/2011 | LaRose et al. | |
| 8,007,254 B2 | 8/2011 | LaRose et al. | |
| 8,152,035 B2 | 4/2012 | Earl | |
| 8,152,493 B2 | 4/2012 | LaRose et al. | |
| 8,323,174 B2 | 12/2012 | Jeevanandam et al. | |
| 8,449,444 B2 | 5/2013 | Poirier | |
| 8,506,471 B2 | 8/2013 | Bourque | |
| 8,562,508 B2 | 10/2013 | Dague et al. | |
| 8,597,350 B2 | 12/2013 | Rudser et al. | |
| 8,636,698 B2 | 1/2014 | Bierman et al. | |
| 8,652,024 B1 | 2/2014 | Yanai et al. | |
| 8,657,733 B2 | 2/2014 | Ayre et al. | |
| 8,668,473 B2 | 3/2014 | LaRose et al. | |
| 9,005,105 B2 | 4/2015 | Yomtov et al. | |
| 9,205,230 B2 | 12/2015 | Rosenberg et al. | |
| 9,242,074 B2 | 1/2016 | Olson | |
| 9,242,115 B2 | 1/2016 | Freeman | |
| 10,589,013 B2 | 3/2020 | Bourque | |
| 2005/0071001 A1 | 3/2005 | Jarvik | |
| 2007/0050005 A1 | 3/2007 | Lauro | |
| 2007/0078293 A1 | 4/2007 | Shambaugh, Jr. et al. | |
| 2008/0021394 A1 | 1/2008 | LaRose et al. | |
| 2008/0300546 A1 | 12/2008 | Godara et al. | |
| 2009/0069812 A1 | 3/2009 | Gillard et al. | |
| 2009/0203957 A1 | 8/2009 | LaRose et al. | |
| 2010/0010449 A1 | 1/2010 | Leibowitz et al. | |
| 2010/0286553 A1 | 11/2010 | Feler et al. | |
| 2011/0196193 A1 | 8/2011 | Forsell | |
| 2012/0045918 A1 | 2/2012 | Litzler et al. | |
| 2012/0046514 A1 | 2/2012 | Bourque | |
| 2012/0046515 A1 | 2/2012 | Woo et al. | |
| 2012/0095281 A1 | 4/2012 | Reichenbach et al. | |
| 2012/0143297 A1 | 6/2012 | Greene | |
| 2013/0096364 A1 | 4/2013 | Reichenbach et al. | |
| 2013/0121821 A1 | 5/2013 | Ozaki et al. | |
| 2013/0127253 A1 | 5/2013 | Stark et al. | |
| 2013/0170970 A1 | 7/2013 | Ozaki et al. | |
| 2013/0225909 A1 | 8/2013 | Dormanen et al. | |
| 2013/0303020 A1 | 11/2013 | Sabin et al. | |
| 2013/0314047 A1 | 11/2013 | Eagle et al. | |
| 2015/0320991 A1 | 11/2015 | Sabin et al. | |
| 2016/0022888 A1 | 1/2016 | Heilman et al. | |
| 2016/0064117 A1 | 3/2016 | Romero et al. | |
| 2016/0129169 A1 | 5/2016 | Forsell | |
| 2018/0200422 A1 | 7/2018 | Nguyen et al. | |

FOREIGN PATENT DOCUMENTS

| | | |
|---|---|---|
| FR | 2970859 | 8/2012 |
| WO | 03090820 A1 | 11/2003 |
| WO | 2009140636 A2 | 11/2009 |

OTHER PUBLICATIONS

Reichenbach et al., "In Vivo Studies of an Implatable Energy Convertor for Skeletal Muscle Powered Cardiac Assist", Reprinted from ASAIO Journal, Published by Lippincott-Raven Publishers, vol. 43, No. 5, © American Society for Artificial Internal Organs, Inc., Sep.-Oct. 1997, 5 pages.

* cited by examiner

DRIVELINE BONE ANCHORS AND METHODS OF USE

CROSS-REFERENCES TO RELATED APPLICATIONS

This application claims the benefit of U.S. Provisional Application No. 62/445,536, filed on Jan. 12, 2017, and entitled "DRIVELINE BONE ANCHORS AND METHODS OF USE", the entirety of which is hereby incorporated by reference herein.

BACKGROUND

This application relates generally to mechanical circulatory support systems, and more specifically relates to control systems, for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure (CHF), may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

Due to VAD workload in constantly pumping blood, VADs can have significantly higher power requirements than other types of implantable devices such as pacemakers or other stimulators. Because of these power requirements, VADs can be externally powered by delivering power from outside of a patient's body to the VAD inside of the patient's body. In many instances, this power can be delivered via a driveline that connects to an external power source and extends into the patient's body to connect with the VAD.

One of the adverse outcomes of VAD therapy is infection. As the driveline transcutaneously extends from the external controller and/or power supply to the implanted blood pump, these infections can be located along the driveline and in many instances can be located where the driveline transcutaneously enters the body. Typically, the driveline includes a material to facilitate tissue ingrowth. In the short term the skin will heal and secure the driveline. In the longer term scar tissue forms to provide a secure stabilizing base for the driveline at the skin line. In some cases, however, the external portion of the driveline is subjected to large forces which are transferred to the skin line resulting in tearing of the tissue. If the force is large enough, the scar tissue can tear. Because scar tissue does not generally regrow over existing scar tissue, the site does not adequately heal and is subject to increased risk of infection. In more problematic cases, the infection can enter the body and subject the patient to further complications. Treating infection can be particularly difficult because CHF patients usually have difficulty healing and suffer from non-cardiac comorbidities like chronic obstructive pulmonary disease (COPD), renal failure, osteoporosis, and osteoarthritis. In some instances, such tears can require expensive and risky readmissions for surgery to properly heal and/or to clear infection, to replace the driveline, or to replace the VAD.

In addition to the risk of infection and problems associated with tearing to the regrown skin, forces applied to the driveline can result in the displacement of the driveline. This displacement can affect tissues and/or organs of the patient in which the VAD is implanted, and in instances in which the displacement is severe, could potentially damage tissues and/or organs. As a result of this, displacement of the driveline can lead to surgery to move the driveline to a desired position and/or to remedy any tissue and/or organ damage caused by the displacement.

Accordingly, there is a need for methods, systems, and devices to address these and other problems. There is a need for methods, systems, and devices to improve stabilization of the driveline. There is a need for improved methods, systems, and devices to decrease the risk of infection associated with the driveline and to decrease the risks arising from displacement and/or movement of the driveline with respect to the patients skin.

BRIEF SUMMARY

Aspects of the present disclosure relate to systems, devices, and method for reducing the risk of infection, tearing of skin surrounding and/or attaching to the driveline, and/or driveline displacement by anchoring the driveline. Such anchoring can result in the rigid or dynamic fixing of the driveline with respect to one or several structures of the patient's body including, for example, one or several bones such as ribs. This anchoring can be achieved via a bone anchor that can attach to and/or be affixed to the driveline and/or to a bone.

Aspects of the present disclosure relate to systems, devices, and methods for anchoring a driveline to a bone. In some embodiments, this bone can be, for example, one or several ribs. The driveline can connect an external controller to an implantable blood pump, and the external controller can provide electrical power and/or control signals to the implantable blood pump. The driveline can extend from the external controller to the blood pump through the patient's skin, and the driveline can be attached to a bone in the patient's body via a bone anchor. In some embodiments, this attachment to the bone can be subcutaneous and/or percutaneous.

The bone anchor can include a driveline capture portion that can receive the driveline and/or a portion of the driveline and fix a position of the driveline relative to the driveline capture portion. The bone anchor can further include a bone capture portion that can engage with a bone and fix the position of the bone capture portion and/or the bone anchor with respect to the bone. In some embodiments, the driveline capture portion and the bone capture portion can be coupled to each other, and more specifically, can be statically coupled to each other. In some embodiments, the bone anchor can couple the driveline to the bone such that forces applied to the driveline are transferred to the bone and not to the skin contacting the driveline. In some embodiments, the bone anchor can couple the driveline such that a force applied to the driveline does not damage and/or tear the skin contacting the driveline and/or damage tissue connected to the implantable blood pump.

One aspect of the present disclosure relates to a bone anchor for securing a driveline to a bone. In some embodiments, the driveline can connect an external controller to an implantable blood pump. The bone anchor includes: a driveline capture portion that can receive the driveline and fix a position of the driveline with respect to the driveline capture portion. The driveline capture portion includes: a driveline receiver that can receive the driveline; and a driveline anchor that can engage the driveline to fix the position of the driveline with respect to the driveline receiver. The bone anchor can include a bone capture portion that can engage a bone and fix a position of the bone with respect to the bone capture portion.

In some embodiments, the driveline receiver defines an aperture. In some embodiments, the aperture has a diameter less than a diameter of the driveline. In some embodiments, the aperture can hold the driveline in a friction fit, and in some embodiments, an inner surface of the aperture can include one or several features that can secure the driveline within the aperture. In some embodiments, the bone anchor has a top, a bottom, a first end, and a second end. In some embodiments, the driveline anchor includes a plurality of capture hooks. In some embodiments, each of the plurality of capture hooks extend towards the top of the bone anchor and are spaced between the first and second ends of the bone anchor.

In some embodiments, at least some of the capture hooks, together with the driveline receiver define a first channel that can hold the driveline in a first orientation. In some embodiments, at least one of the capture hooks, together with the driveline receiver defines a second channel that can hold the driveline in a second orientation. In some embodiments, the driveline in the first orientation is perpendicular to the driveline in the second orientation. In some embodiments, the bone capture portion comprises can be screw, a U-bolt, a U-channel, and/or a cable tie. In some embodiments, the bone capture portion includes a first U-member comprising a base and a second U-member comprising a base and a top, wherein the bases of the first and second U-members are connected.

One aspect of the present disclosure relates to a system for securing a driveline to a bone via a bone anchor. In some embodiments, the driveline electrically connects an external controller and an implantable blood pump. The system includes: an implantable blood pump having a rotor and a stator; an external controller that can power the implantable blood pump and provide a control signal to the implantable blood pump; a percutaneous driveline electrically connecting the implantable blood pump and the external controller, which percutaneous driveline has a diameter; and a bone anchor. The bone anchor can include: a driveline capture portion that can receive the driveline and fix a position of the driveline with respect to the driveline capture portion; and a bone capture portion that can receive a bone and fix a position of the bone with respect to the driveline capture portion.

In some embodiments, the driveline receiver defines an aperture having a diameter less than the diameter of the percutaneous driveline. In some embodiments, the bone capture portion can include an elongate member and at least one screw extending through a portion of the elongate member. In some embodiments, the bone capture portion includes an elongate member having a first end, a second end, a top, and a bottom, and which bone capture portion includes a first screw hole proximate to the first end and a second screw hole proximate to the second end.

In some embodiments, the bone capture portion can be a U-shaped elongate member having a top, an open bottom, a first end, and a second end. In some embodiments, the driveline anchor can include a plurality of capture hooks extending from the top of the U-shaped elongate member. In some embodiments, the plurality of hooks include a first hook in a first orientation and a second hook in a second orientation. In some embodiments, the first and second hooks together with top of the U-shaped elongate member define a first channel that can hold the driveline in a first orientation. In some embodiments, the driveline anchor further includes a third hook in a third orientation. In some embodiments, the third hook together with top of the U-shaped elongate member defines a second channel configured to hold the driveline in a second orientation. In some embodiments, the driveline in the first orientation is perpendicular to the driveline in the second orientation.

One aspect of the present disclosure relates to a method for affixing a driveline to a bone. In some embodiments, the driveline electrically connects an external controller to an implantable blood pump. The method includes: implanting the implantable blood pump in a patient's body; creating a driveline path through a patient's body, which driveline path passes at least one desired bone; and connecting the driveline to a bone anchor via a driveline capture portion that can receive the driveline and fix a position of the driveline with respect to the driveline capture portion. In some embodiments, the driveline capture portion includes: a driveline receiver that can receive the driveline; and a driveline anchor that can the driveline to fix the position of the driveline with respect to the driveline receiver. The method includes: connecting the bone anchor to the at least one desired bone via a bone capture portion that can engage a bone and fix a position of the bone with respect to the bone capture portion; and electrically connecting the external controller and the implantable blood pump.

In some embodiments, connecting the driveline to the bone anchor via the driveline capture portion includes receiving the driveline in the driveline receiver and fixing the position of the driveline with respect to the driveline receiver via the driveline anchor. In some embodiments, the driveline receiver defines an aperture comprising a diameter less than a diameter of the driveline. In some embodiments, the bone anchor has a top, a bottom, a first end, and a second end, and In some embodiments, the driveline anchor includes a plurality of capture hooks. In some embodiments, fixing the position of the driveline with respect to the driveline receiver via the driveline anchor includes inserting the driveline through the plurality of capture hooks. In some embodiments, each of the plurality of capture hooks extend towards the top of the bone anchor and are spaced between the first and second ends of the bone anchor.

In some embodiments, at least some of the capture hooks, together with the driveline receiver define a first channel configured to hold the driveline in a first orientation. In some embodiments, at least one of the capture hooks, together with the driveline receiver defines a second channel configured to hold the driveline in a second orientation. In some embodiments, the driveline in the first orientation is perpendicular to the driveline in the second orientation. In some embodiments, electrically connecting the external controller and the implantable blood pump includes providing at least one of: power; or a control signal to the implantable blood pump via the driveline.

The preceding presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later. For a fuller understanding of the nature and advantages of the present invention, reference should be made to the ensuing detailed description and accompanying drawings.

DETAILED DESCRIPTION

A driveline of a VAD can connect the VAD to an external controller or external power source. Some embodiments of such a driveline are disclosed in U.S. Pat. No. 9,603,984, filed on Sep. 3, 2015, and entitled "TRIPLE HELIX DRIVELINE CABLE AND METHODS OF ASSEMBLY AND USE", the entirety of which is hereby incorporated by reference herein. Such drivelines can facilitate providing the significantly higher amount of power used in operation of the VAD as compared to other types of implantable devices such as pacemakers or other stimulators. However, the driveline can cause problems as the driveline transcutaneously extends through the skin. This can increase risk of infection. Further, movement of the driveline with respect to the patient's skin such as by the application of a force to the driveline can result in the tearing of skin and/or separation of skin from the drive, and/or can increase the risk of infection.

In addition to this, because the driveline is connected to the implantable blood pump, forces applied to the driveline can be transferred to the implantable blood pump and to the tissue and/or organ to which the implantable blood pump is connected. If sufficiently large forces are applied to the implantable blood pump via the driveline, this could result in damage to the tissue and/or organ to which the implantable blood pump is connected and/or to the separation of the implantable blood pump from that tissue and/or organ. Certain aspects of the inventions described herein are directed to reducing the risk of movement of the driveline. Various embodiments are directed to limiting movement of the driveline within a predetermined range, e.g., to mitigate the risk of tearing. The movement can be at the skin line, within the body (e.g. at the pump, or both. In various embodiments, the driveline resists any movement. A significantly higher force is applied to any movement beyond the desired and/or implant position. In various embodiments, the driveline is subjected to increased or step-change resistance outside of a proscribed range. The proscribed range may be determined by the anatomy and/or clinical context.

Some embodiments of the present disclosure address the above risks by a bone anchor that anchors the driveline to a bone in the patient's body, and specifically to a bone in the patient's body that is static and/or adequately static with respect to the skin surrounding the insertion point of the driveline and/or to the tissue and/or organ to which the implantable blood pump is connected. In some embodiments, these bone anchors can attach to a rib proximate to the point of insertion of the driveline into the patient's body. These bone anchors can attach to the bone via one or several bone screws, clamping members, U-shaped members, or the like.

Figure 1:
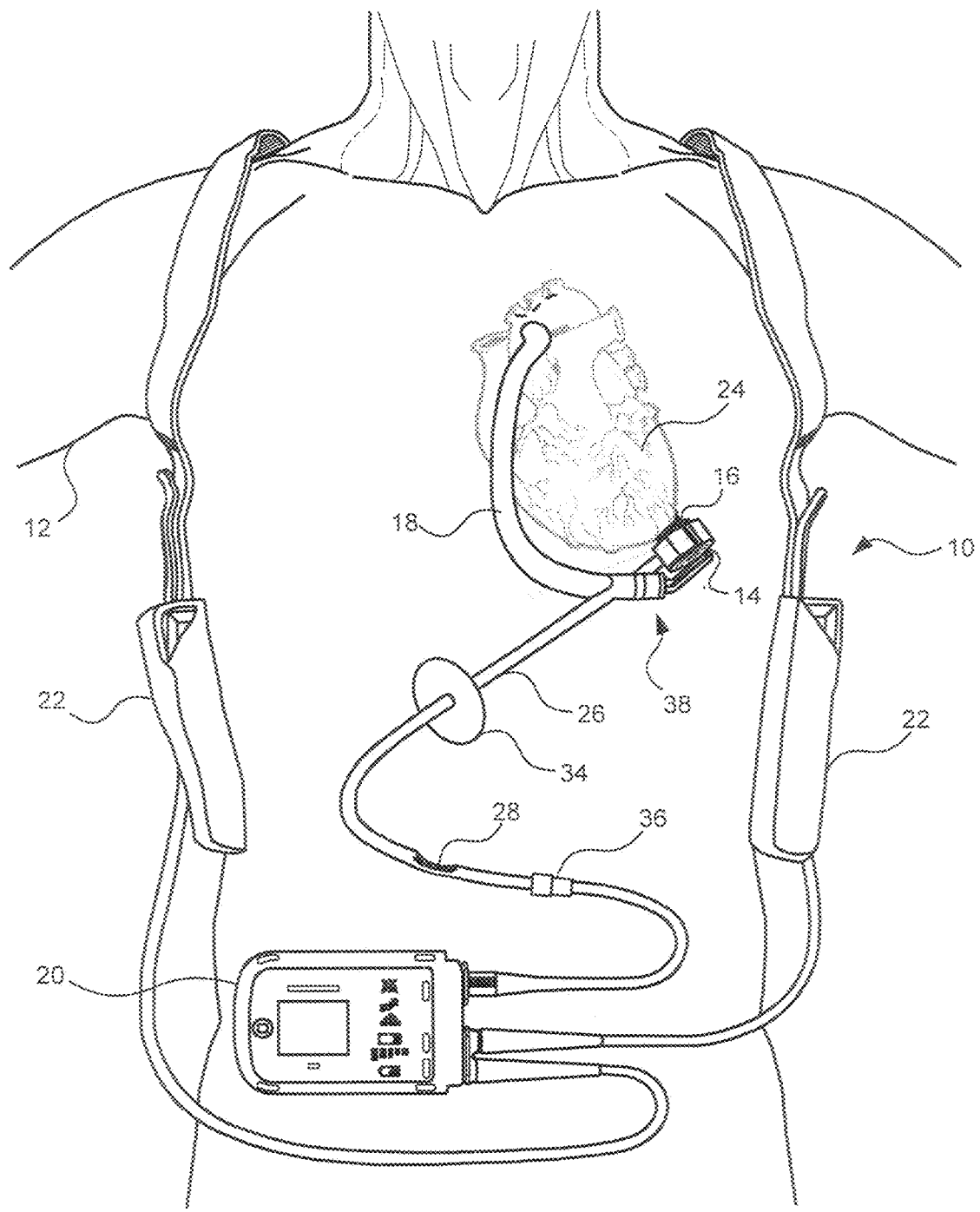
FIG. 1 is an illustration of a mechanical circulatory support system implanted in a patient's body.
Figure 2:
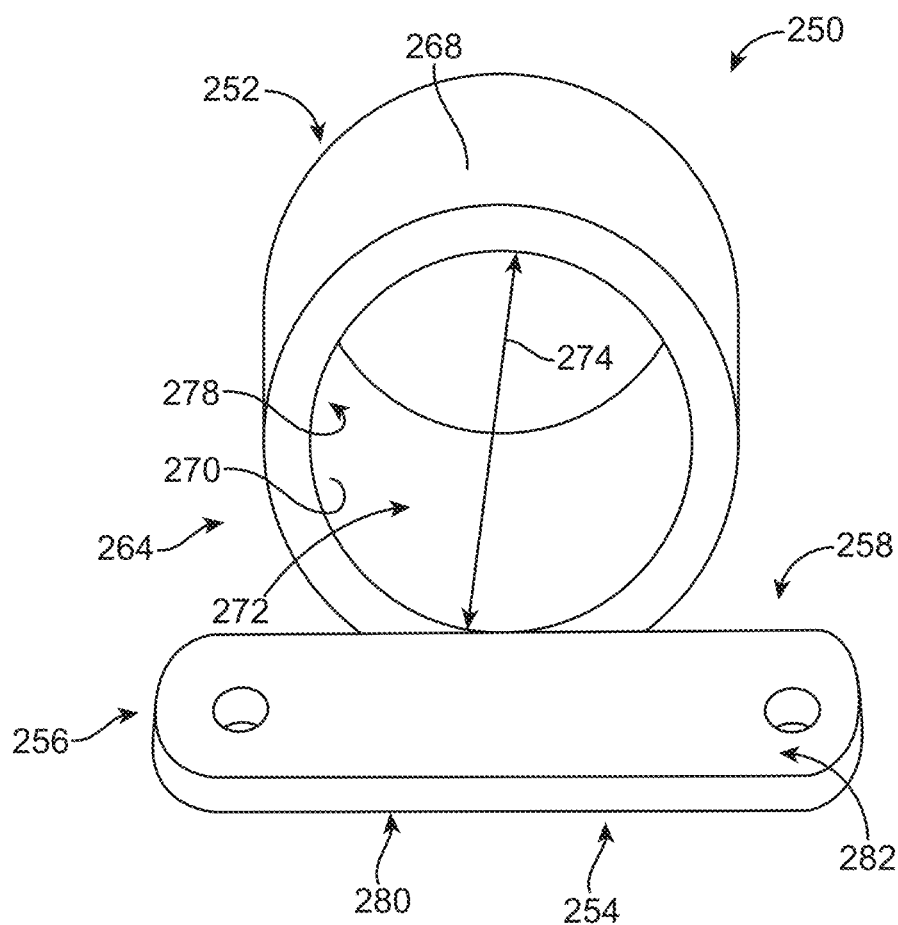
FIG. 2 is a perspective view of one embodiment of a bone anchor comprising an aperture.

Referring now to the drawings, in which like reference numerals represent like parts throughout the several views, FIG. 1 is an illustration of a mechanical circulatory support system 10 implanted in a patient's body 12. The mechanical circulatory support system 10 comprises an implantable blood pump 14, ventricular cuff 16, outflow cannula 18, system controller 20, and external power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, 8,668,473, 8,419,609 7,976,271, 8,852,072, 9,091,271, 9,265,870, 8,864,643, 9,382,908, 9,068,572, 8,882,744, all of which are incorporated herein by reference for all purposes in their entirety. With reference to FIGS. 1 and 2, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during external power source 22 powered operation. A driveline 26 which exits through the patient's abdomen 28, connects the implanted blood pump 14 to the system controller 20, which monitors system 10 operation. In some embodiments, the driveline 26 exits the body via a port 34 in the skin of the patient. In some embodiments, the driveline 26 can include an external connector 36 which can be located outside of the patient's body and which can separate the driveline 26 into a first piece that connects to the implanted or implantable blood pump 14 and a second piece that connects to the system controller 20. In some embodiments, the driveline 26 can connect to the implanted blood pump 14 in a hermetically sealed housing 38. In some embodiments, the driveline 26 can be a percutaneous driveline which can electrically connect the implantable blood pump 14 to the system controller 20, also referred to herein as the external controller 20. In some embodiments, the implantable blood pump 14 can include a rotor and a stator and the external controller 20 can power the implantable blood pump 14 and provide one or several control signals to the implantable blood pump 14.

Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more external power sources 22. It will be appreciated that although the system controller 20 and power source 22 are illustrated outside/external to the patient body, the driveline 26, system controller 20 and/or power source 22 may be partially or fully implantable within the patient, as separate components or integrated with the blood pump 14. Examples of such modifications are further described in U.S. Pat. No. 8,562,508 and U.S. Patent Publication No. 2013/0127253, all of which are incorporated herein by reference for all purposes in their entirety.

Figure 3:
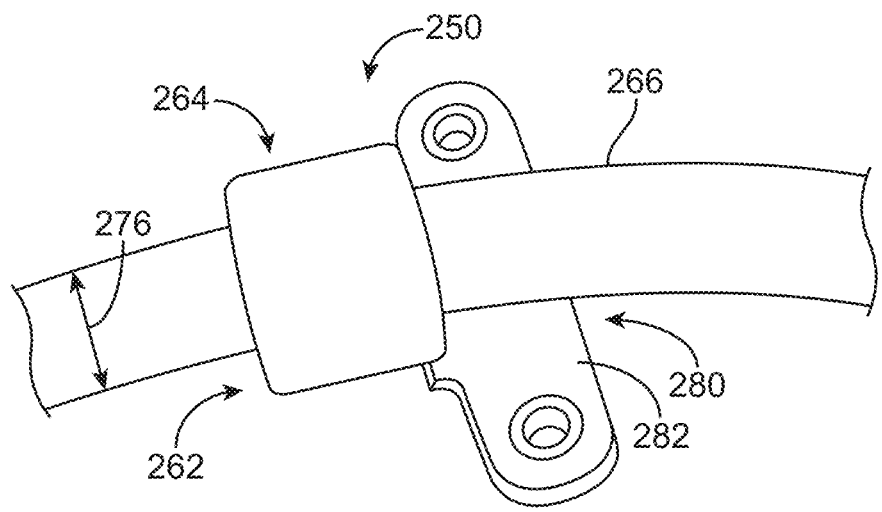
FIG. 3 is a perspective view of one embodiment of a bone anchor comprising an aperture with an inserted driveline.

With reference now to FIGS. 2 and 3, perspective views of one embodiment of a bone anchor 250 is shown. The bone anchor 250 can include features configured to engage with a bone and engage with the driveline. The bone anchor 250 includes a top 252, a bottom 254, a first side 256 (also referred to herein as a first end 256), a second side 258 (also referred to herein as a second end 258), a front 260 and a back 262. The bone anchor further includes a driveline capture portion 264 that is configured to receive a driveline 266. The driveline capture portion 264 can be further configured to fix a position of the driveline 266 with respect to the driveline capture portion 264. As used herein, fixing the position of the driveline can refer to limiting motion entirely or within a proscribed range. In various respects, fixing and anchoring are used somewhat interchangeably.

The driveline capture portion 264 includes a driveline receiver 268 that receives the driveline 266 and a driveline anchor 270 that engages the driveline 266 to fix the position of the driveline 266 with respect to the driveline anchor 270, the driveline receiver 268, and/or the driveline capture portion 264.

In some embodiments, the driveline receiver 268 can define a feature such as a channel or aperture that can receive the driveline 266. As specifically shown in FIG. 2, in some embodiments, the driveline receiver 268 defines an aperture 272 can be, for example, a circular or cylindrical aperture. In some embodiments, the aperture 272 can have a diameter 274. The diameter 274 can be sized with respect to a diameter 276 of the driveline 266, as shown in FIG. 3, such that the driveline 266 can be received within the aperture 272.

In some embodiments, the diameter 274 of the aperture 272 can be greater than the diameter 276 of the driveline 266, can be equal to the diameter 276 of the driveline 266, or can be less than the diameter 276 of the driveline 266. In some embodiments, the diameter 274 of the aperture 272 can be selected to create a friction fit between the driveline 266 and the inner surface 278 of the aperture 272. In some embodiments, this can result in the elastic deformation of all or portions of the driveline receiver 268 and/or the driveline 266 when the driveline 266 is inserted into and/or through the aperture 272.

In some embodiments, the diameter 274 of the aperture 272 can be selected so that an inner surface 278 of the aperture 272, which inner surface can be the driveline anchor 270, engages with the drive line 266 to secure the position of the driveline 266 with respect to the aperture 272. In some embodiments, this inner surface 278 of the aperture 272 can comprise one or several features and/or materials that interact with the driveline 266 to prevent movement of the driveline 266 with respect to the aperture 272. In some embodiments, these one or several features of the inner surface 278 can include, for example, a textured surface, a pitted surface, one or several ribs, one or several grooves, or the like. In some embodiments, these materials can include a high friction material, adhesive, is sticky and/or tacky material, rubber, a deformable material, or the like.

The bone anchor 250 can further include a bone capture portion 280. The bone capture portion can engage a bone and fix a position of the bone with respect to the bone anchor 250 and/or the driveline capture portion 264. In some embodiments, the bone capture portion 280 can statically fix a position of the bone with respect to the driveline capture portion 264 and in some embodiments, the bone capture portion 280 can dynamically fix the position of the bone with respect to the driveline capture portion 264. In some embodiments, for example, the driveline capture portion 264 and the bone capture portion 280 can be connected by one or several rigid elements and in some embodiments, the driveline capture portion 264 and the bone capture portion 280 can be connected by one or several elastic elements such as, for example one or several springs. In various embodiments, the elastic elements are configured to provide a linear spring force against movement. In various embodiments, the elastic elements are configured to provide a stronger force after a certain degree of movement.

In some embodiments, and as depicted in FIGS. 2 and 3, the bone capture portion 280 can comprise an elongate member 282 extending from the first end 256 to the second end 258. The elongate member 282 can include one or several features configured to receive one or several screws and/or can include one or several screws. In some embodiments, these one or several screws can comprise one or several bone screws that can be, for example, self-tapping.

Figure 4:
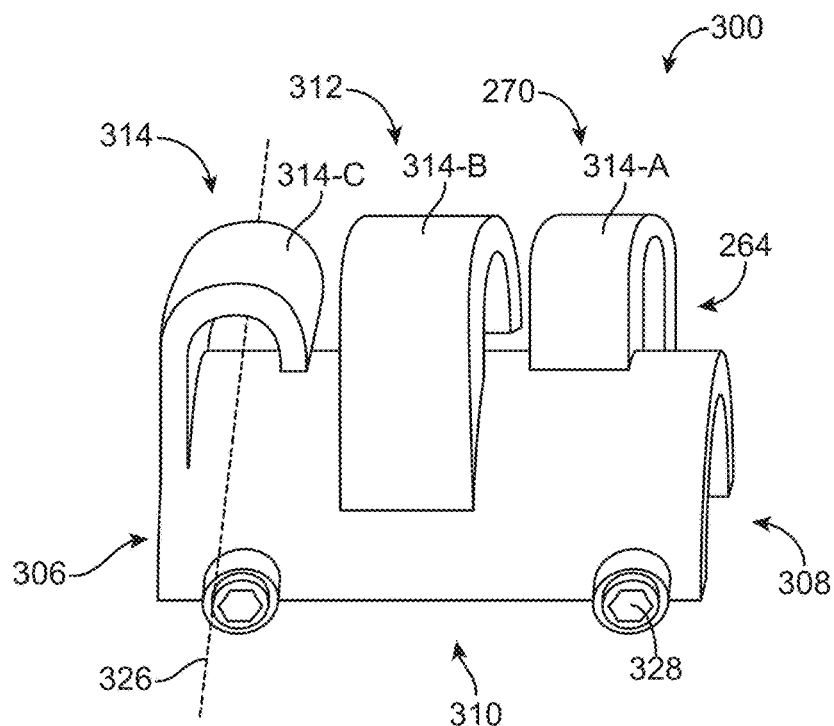
FIG. 4 is a perspective view of one embodiment of a bone anchor comprising a plurality of capture hooks in three orientations.
Figure 5:
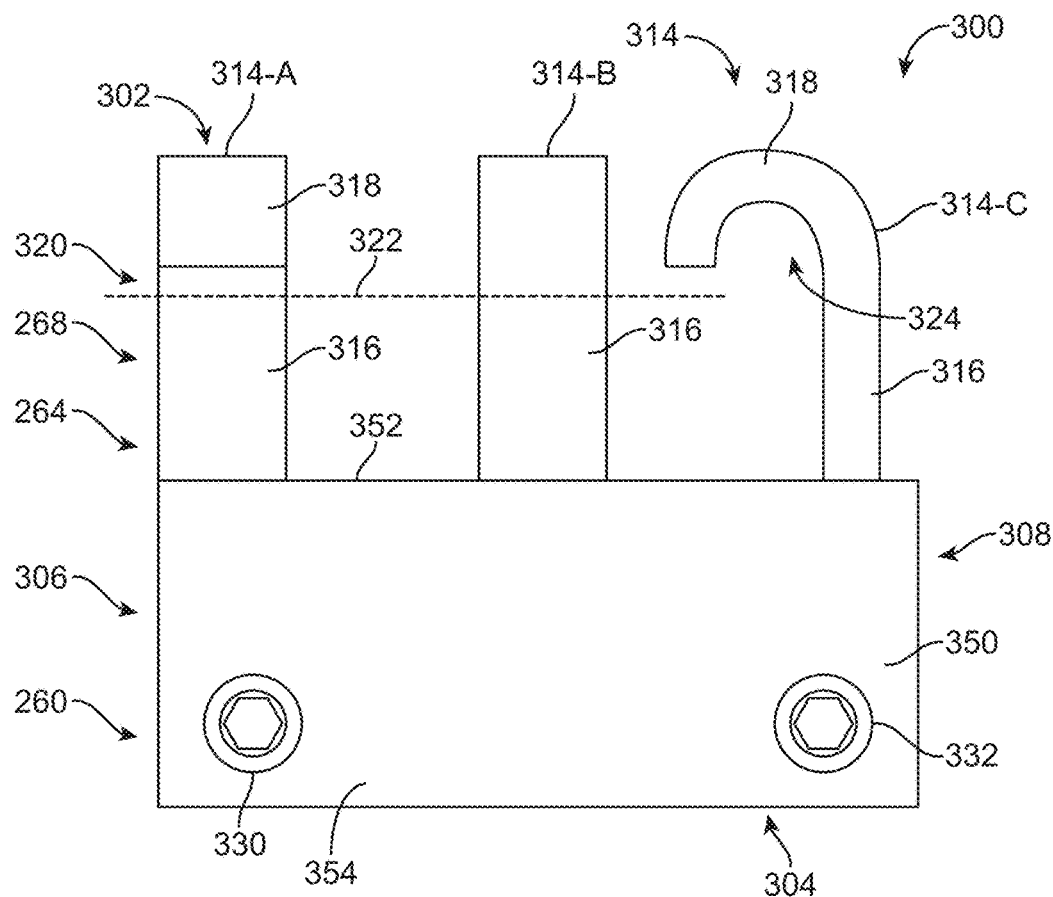
FIG. 5 is a front view of one embodiment of a bone anchor comprising a plurality of capture hooks in three orientations.
Figure 6:
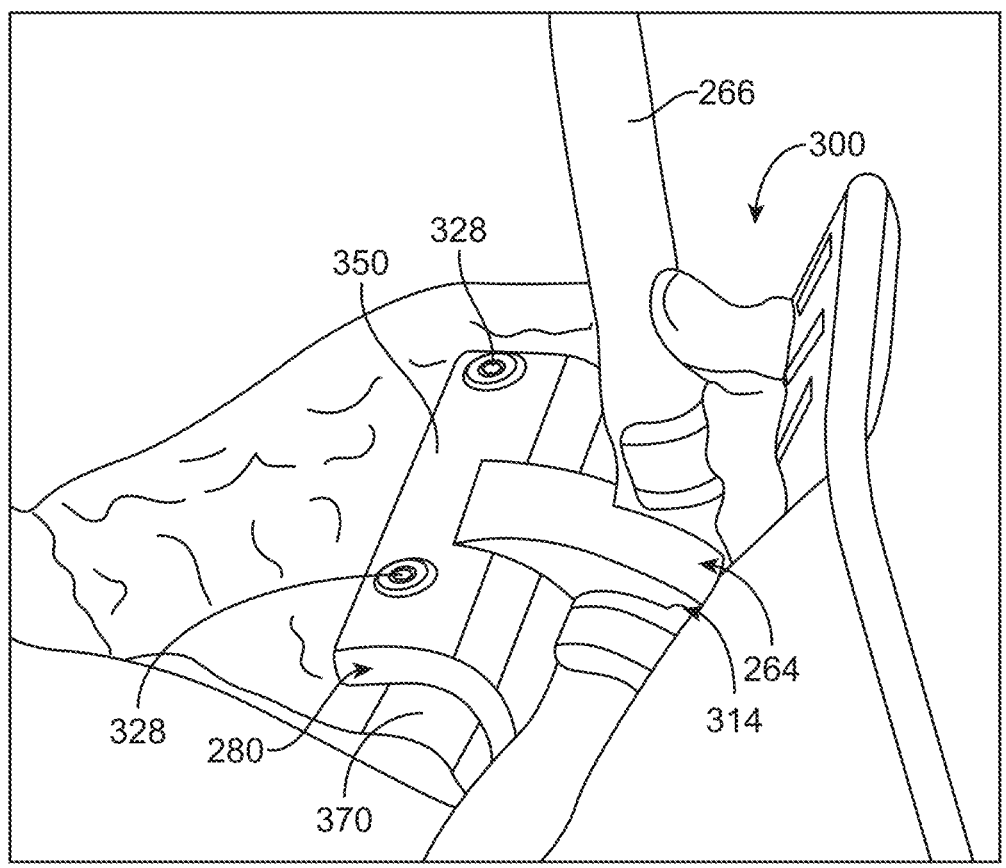
FIG. 6 is a perspective view of one embodiment of a bone anchor comprising a plurality of capture hooks in three orientations attached to a bone.

With reference now to FIGS. 4 through 6, perspective views of one embodiment of a bone anchor 300 is shown. The bone anchor 300 can include features configured to engage with a bone and engage with the driveline. The bone anchor 300 includes a top 302, a bottom 304, a first side 306 (also referred to herein as a first end 306), a second side 308 (also referred to herein as a second end 308), a front 310 and a back 312.

The bone anchor 300 can comprise an elongate body 350 that can have a top 352, a bottom 354, and extend from the first end 306 to the second end 308. The elongate body 350 can comprise a variety of shapes and sizes and can be made from a variety of materials. In some embodiments, the elongate body 350 can comprise a U-shaped member 356 having a first terminating edge 358 and the second terminating edge 360. In some embodiments, one or both of the first and second terminating edges 358, 360 can be located at and/or proximate to the bottom 354 of the elongate body 350 such that the bottom 354 of the elongate body 350 is open.

As seen in FIGS. 4 and 5, the bone anchor 300 can comprise a plurality of capture hooks 314 space between the first and second ends 306, 308 of the bone anchor 300 and extending from the top 352 of the elongate member 350 towards the top 302 of the bone anchor. In some embodiments this can include, for example, a first hook 314-A, a second hook 314-B, and a third hook 314-C. Each of the plurality of capture hooks 314 can include a shaft portion 316 and a hook portion 318. In some embodiments, some or all of the capture hooks 314 can, together with portions of the elongate body 350, define one or several channels configured to hold the driveline 266.

As seen in FIGS. 4 and 5, some of the capture hooks 314, and specifically the first capture hook 314-A and the second hook 314-B, can together with the elongate body 350 define a first channel 320 along a first axis 322 and at least one of the capture hooks 314, and specifically the third capture hook 314-C can together with the elongate body 350 define a second channel 324 along a second axis 326. In some embodiments, the first channel 320 can be configured to hold the driveline 266 in a first orientation and the second channel 324 can be configured to hold the driveline 266 and a second orientation. In some embodiments, the first orientation of the driveline 266 can be angled with respect to the second orientation of the driveline 266, and in some embodiments, the first orientation of the driveline 266 can be perpendicular to the second orientation of the driveline 266. In some embodiments, one or both of the first channel 320 and the second channel 324 can be sized and shaped to engage with and/or hold the driveline 266 in a fixed position with respect to the capture hooks 314 and/or the bone anchor 300.

In some embodiments, the first hook 314-A can be in a first orientation, the second hook 314-B can be in a second orientation, and the third hook 314-C can be in a third orientation. In some embodiments, some or all of the first, second, and third orientations are different. In the embodiment depicted in FIGS. 4 through 6, the first orientation of the first hook 314-A is the mirror of the second orientation of the second hook 314-B. In some embodiments, the shaft portion 316 of first hook 314-A can connect to the back 312 of the bone anchor 300 and the shaft portion 316 of the second hook 314-B can connect to the front 310 of the bone anchor 300. In this configuration, the mirrored orientations of the first hook 314-A in the second hook 314-B results in the creation of the first channel 320 along the first axis 322.

The bone anchor further includes a driveline capture portion 264 that is configured to receive a driveline 266. The driveline capture portion 264 can be further configured to fix a position of the driveline 266 with respect to the driveline capture portion 264. The driveline capture portion 264 includes a driveline receiver 268 that receives the driveline 266 and a driveline anchor 270 that engages the driveline 266 to fix the position of the driveline 266 with respect to the driveline anchor 270, the driveline receiver 268, and/or the driveline capture portion 264. In some embodiments, the driveline receiver 268 can include the top 352 of the elongate body 350 and in some embodiments, the driveline anchor 270 can include the plurality of capture hooks 314.

The bone anchor 300 can further include the bone capture portion 280 which can include portions of the elongate member 350 and, for example, a least one screw 328 extending through a portion of the elongate member 350. In some embodiments, the bone capture portion 280 can include all or portions of the elongate member 350 and a first screw hole 330 proximate to the first end 306 of the bone anchor 300 and a second screw hole 332 proximate to the second end 308 of the bone anchor 300.

FIG. 6 depicts a perspective view of the bone anchor 300 attached to a bone 370. In some embodiments, the bone anchor can be connected to the driveline 266, and specifically to the driveline capture portion 264 of the bone anchor. In some embodiments, this can include the receipt of the driveline within the driveline receiver and the fixing of the position of the driveline with respect to the driveline receiver by the driveline anchor. The bone anchor can be connected to the bone 370 via the bone capture portion of the bone anchor. In some embodiments, the bone capture portion can engage a bone 370 and fix the position of the bone with respect to the driveline anchor.

As specifically seen in FIG. 6, the driveline capture portion 264 can fix the position of the driveline 266 via the plurality of capture hooks 314 which connect the driveline capture portion 264 two the bone capture portion 280. As seen, the bone anchor 300 comprises the elongate member 350 which is a U-shaped elongate member and the bone 370 is received within the U-shaped elongate member. The bone 370 is secured via the screws 328 that extend through a portion of the elongate member 350 and into the bone 370.

Figure 7:
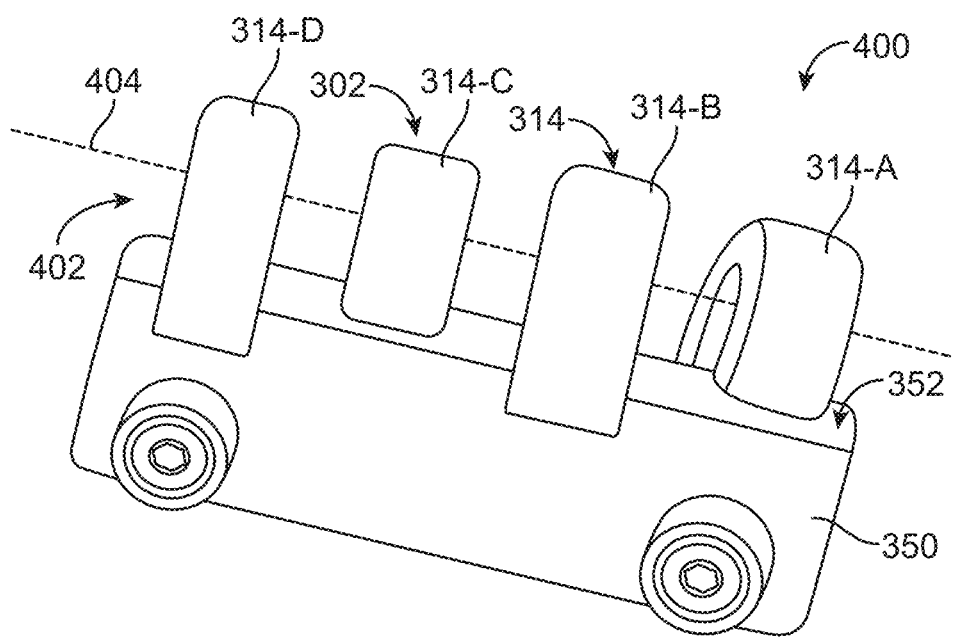
FIG. 7 is a perspective view of one embodiment of a bone anchor comprising a plurality of capture hooks in two orientations.

With reference now to FIG. 7, a perspective view of one embodiment of a bone anchor 400 is shown. The bone anchor 400 is similar to the bone anchor 300 in that the bone anchor 400 comprises a plurality of capture hooks 314 extending from the top 352 of the elongate member 350 towards the top 302 of the bone anchor 400. As further seen in FIG. 7, the plurality of capture hooks 314 include a first capture hook 314-A in a first orientation, a second capture hook 314-B in the second orientation, a third capture hook 314-C in the first orientation, and a fourth capture hook 314-D in the second orientation. As further seen in FIG. 7, the second orientation is the mirror of the first orientation such that the plurality of capture hooks 314 together define a channel 402 having an axis 404. In some embodiments, the channel 402 can be sized such that the capture hooks 314 engage with and hold the driveline 266.

Figure 8:
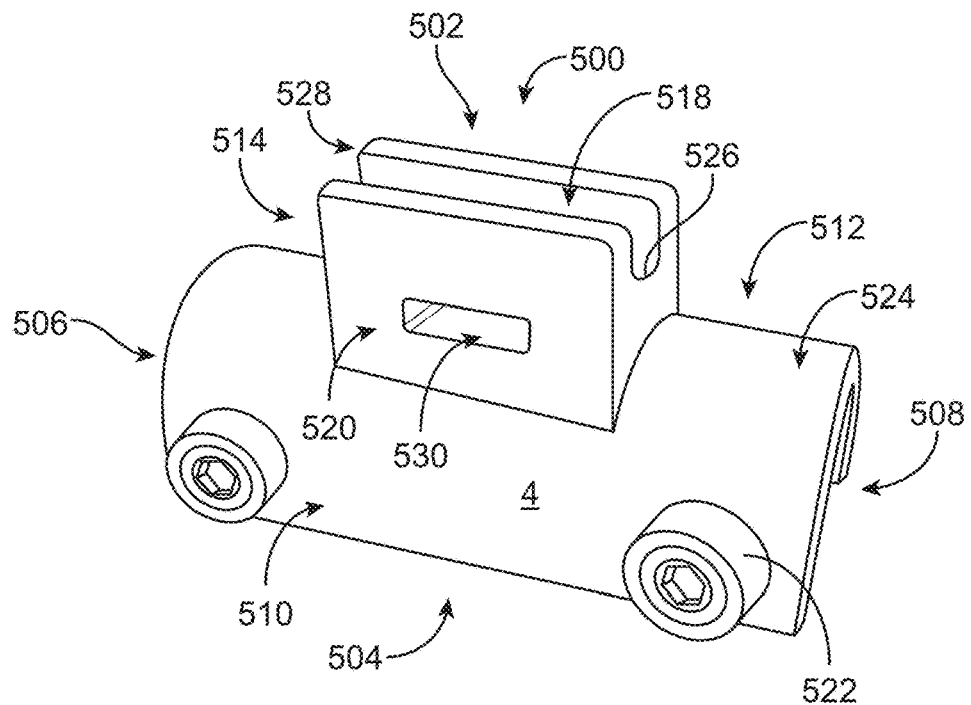
FIG. 8 is a perspective view of one embodiment of a bone anchor comprising an aperture for receiving a cable tie.

With reference now to FIG. 8, a perspective view of one embodiment of a bone anchor 500 is shown. The bone anchor 500 can include features configured to engage with a bone and engage with the driveline. The bone anchor 500 includes a top 502, a bottom 504, a first side 506 (also referred to herein as a first end 506), a second side 508 (also referred to herein as a second end 508), a front 510 and a back 512. The bone anchor further includes a driveline capture portion 514 that is configured to receive a driveline 266. The driveline capture portion 514 can be further configured to fix a position of the driveline 266 with respect to the driveline capture portion 514.

The driveline capture portion 514 includes a driveline receiver 518 that receives the driveline 266 and a driveline anchor 520 that engages the driveline 266 to fix the position of the driveline 266 with respect to the driveline anchor 520, the driveline receiver 518, and/or the driveline capture portion 514.

The bone anchor 500 further comprises an elongate member 522 that can comprise a U-shaped elongate member. The elongate member 522 comprises a top 524 intermediate between the top 502 and the bottom 504 of the bone anchor 500. In some embodiments, the driveline capture portion 514 can extend from the top 524 of the elongate member 522. Specifically, driveline receiver 518 of the driveline capture portion 514 comprises a pedestal 526 extending from the top 524 of the elongate member 522 to the top 502 of the bone anchor 500. The pedestal 526 defines a receiving channel 528 at the top 502 of the bone anchor 500, which receiving channel 528 is sized and shaped to receive the driveline 266.

In some embodiments, the driveline anchor 520 can comprise an aperture 530 located in the pedestal 526 between all or portions of the receiving channel 528 and the top 524 of the elongate member 522. In some embodiments, the aperture 530 can be sized and shaped to receive and retain a fastener such as a mechanical and/or adhesive fastener to secure the driveline 266 within the receiving channel 528. In some embodiments, this fastener can comprise, for example, a cable tie or tie-wrap, which cable tie or tie-wrap. In some embodiments, for example, the driveline 266 can be positioned within the receiving channel 528, and the cable tie or tie-wrap can be inserted through the aperture 530 and around the driveline 266. The cable tie or tie-wrap can then be tightened on the driveline 266 to secure the position of the driveline 266 with respect to the bone anchor 500.

Figure 9:
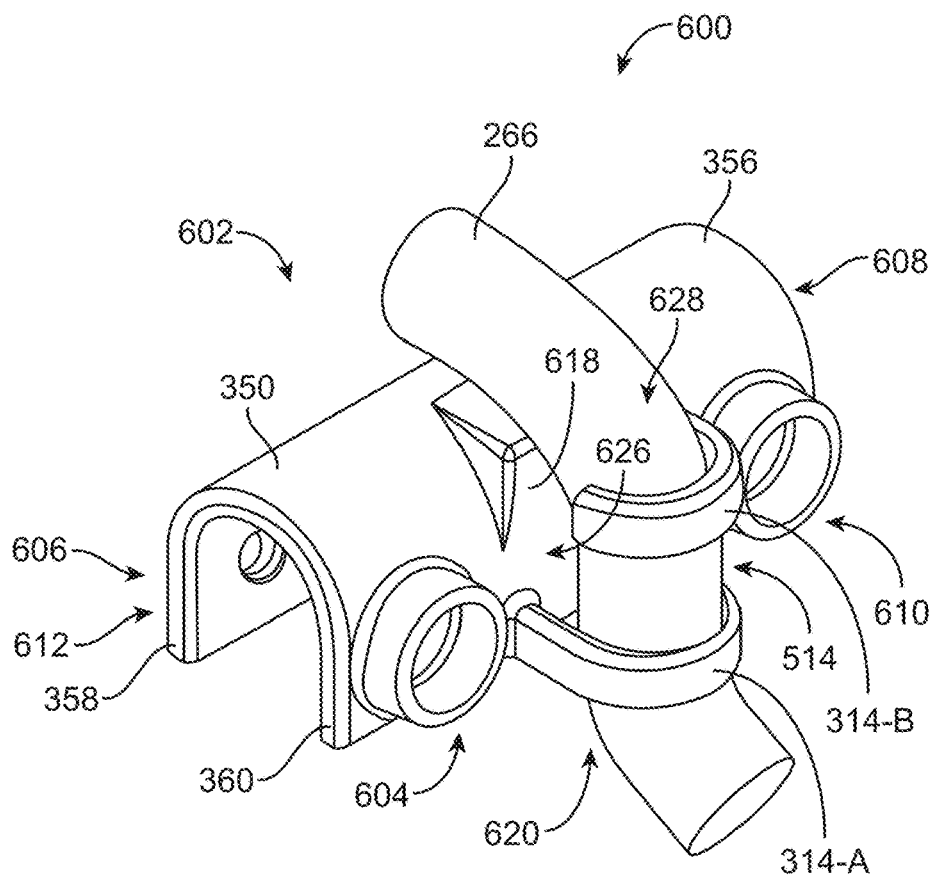
FIG. 9 is a perspective view of one embodiment of a bone anchor comprising a two capture hooks in two orientations.

With reference now to FIG. 9 a perspective view of one embodiment of a bone anchor 600 is shown. The bone anchor 600 can include features configured to engage with a bone and engage with the driveline. The bone anchor 600 includes a top 602, a bottom 604, a first side 606 (also referred to herein as a first end 606), a second side 608 (also referred to herein as a second end 608), a front 610 and a back 612. The bone anchor further includes a driveline capture portion 614 that is configured to receive a driveline 266. The driveline capture portion 614 can be further configured to fix a position of the driveline 266 with respect to the driveline capture portion 614.

The driveline capture portion 614 includes a driveline receiver 618 that receives the driveline 266 and a driveline anchor 620 that engages the driveline 266 to fix the position of the driveline 266 with respect to the driveline anchor 620, the driveline receiver 618, and/or the driveline capture portion 614.

The bone anchor 600 further comprises an elongate member 350 that can comprise a U-shaped elongate member. In some embodiments, the elongate body 350 can comprise a U-shaped member 356 having a first terminating edge 358 and the second terminating edge 360. In some embodiments, one or both of the first and second terminating edges 358, 360 can be located at and/or proximate to the bottom 354 of the elongate body 350 such that the bottom 354 of the elongate body 350 is open.

In some embodiments, the driveline capture portion 614 can extend from the front 610 of the elongate member 350. Specifically, driveline receiver 618 of the driveline capture portion 614 comprises a surface 626 extending from the front 612 of the elongate member 522. The surface 626 is sized and shaped to receive the driveline 266. The driveline anchor 620 can comprise a plurality of capture hooks 314 extending from the surface 626. The capture hooks 314 can include, a first capture hook 314-A having a first orientation and a second capture hook 314-B having a second orientation. In some embodiments, the capture hooks 314 can, with the surface 626 define a channel 628 extending through both of the capture hooks 314, which channel 628 can be sized and shaped to receive the driveline 266 and to engage the driveline 266 to fix the position of the driveline 266 with respect to the surface 626.

Figure 10:
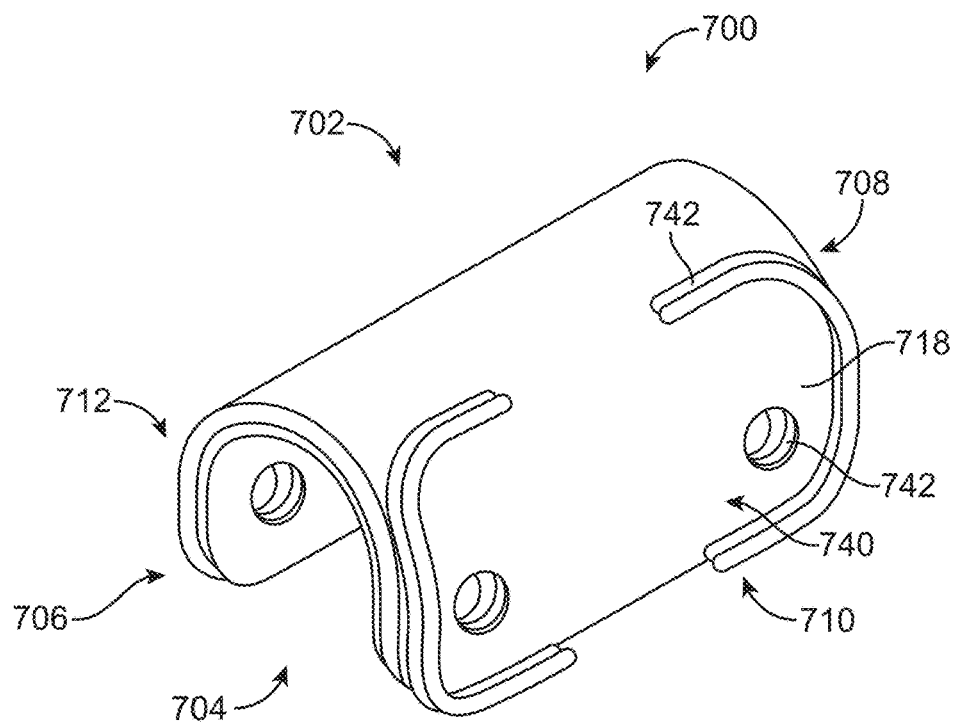
FIG. 10 is a perspective view of one embodiment of a bone anchor comprising a front portion for receiving a plate member.
Figure 11:
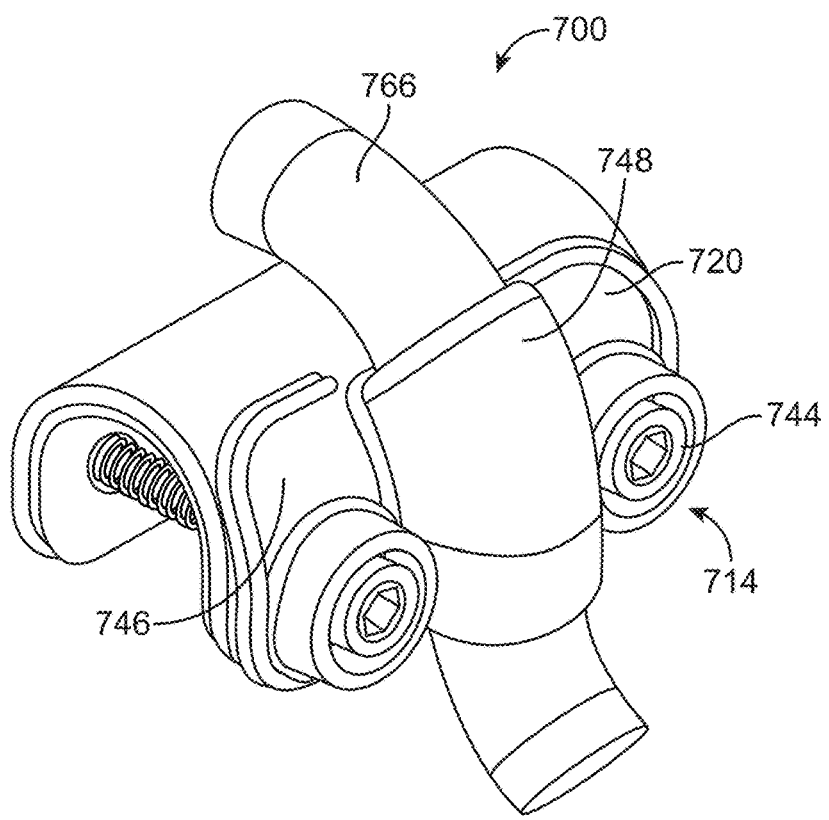
FIG. 11 is a perspective view of one embodiment of a bone anchor with a plate member attached to a front portion.

With reference now to FIGS. 10 and 11, perspective views of one embodiment of the bone anchor 700 is shown. The bone anchor 700 can include features configured to engage with a bone and engage with the driveline. The bone anchor 700 includes a top 702, a bottom 704, a first side 706 (also referred to herein as a first end 706), a second side 708 (also referred to herein as a second end 708), a front 710 and a back 712. The bone anchor further includes a driveline capture portion 714 that is configured to receive a driveline 266. The driveline capture portion 714 can be further configured to fix a position of the driveline 266 with respect to the driveline capture portion 714.

The driveline capture portion 714 includes a driveline receiver 718 that receives the driveline 266 and a driveline anchor 720 that engages the driveline 266 to fix the position of the driveline 266 with respect to the driveline anchor 720, the driveline receiver 718, and/or the driveline capture portion 714. The driveline receiver 718 comprises a front portion 740 on the elongate member 350, which can comprise a U-shaped elongate member, of the bone anchor 700. In some embodiments, the front portion 740 can comprises one or several location features configured to engage with the driveline anchor 720 to facilitate proper attachment of the driveline anchor 720 to the elongate member 350. In some embodiments, the front portion 740 further comprises one or several screw holes 742 configured to receive one or several screws 744 to secure the driveline anchor 720 to the elongate member 350 and/or to secure the bone anchor 700 to the bone.

In some embodiments, the driveline anchor can comprise a plate member 746 that is attachable to the elongate body 350, and particularly to the front portion 740. The plate member 746 can comprise a channel portion 748 that can receive the driveline 266 and that can secure the position of the driveline with respect to the front portion 740 by, for example, compressing the driveline 266 between the front portion 740 and the plate member 746 when the plate member 746 is connected to the front portion 740.

Figure 12:
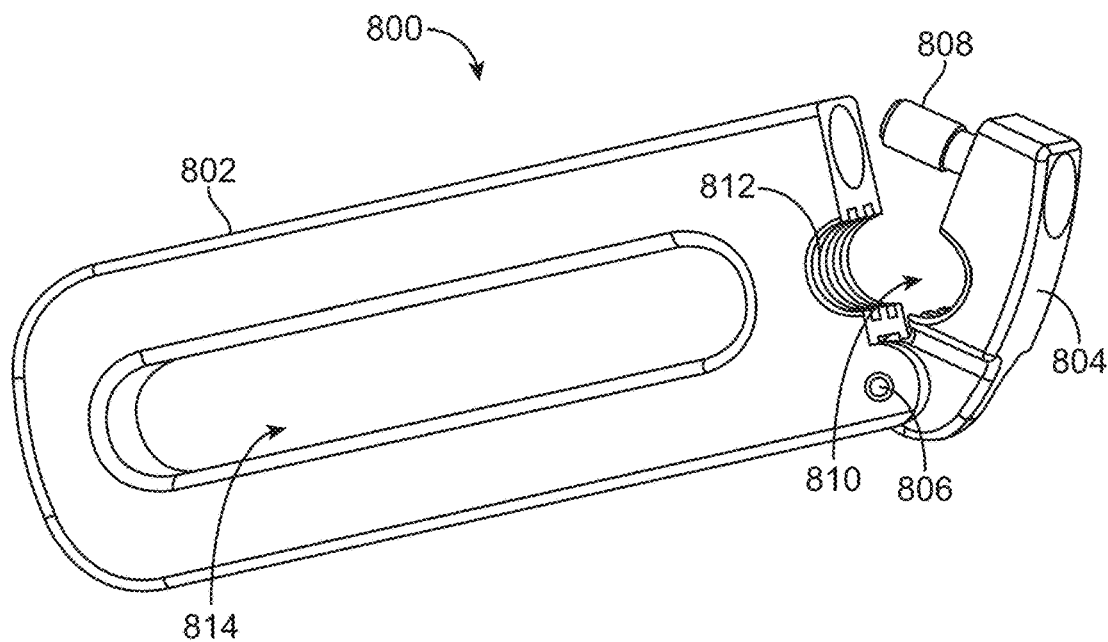
FIG. 12 is a perspective view of one embodiment of a driveline capture portion comprising an elongate body of a bone anchor.
Figure 13:
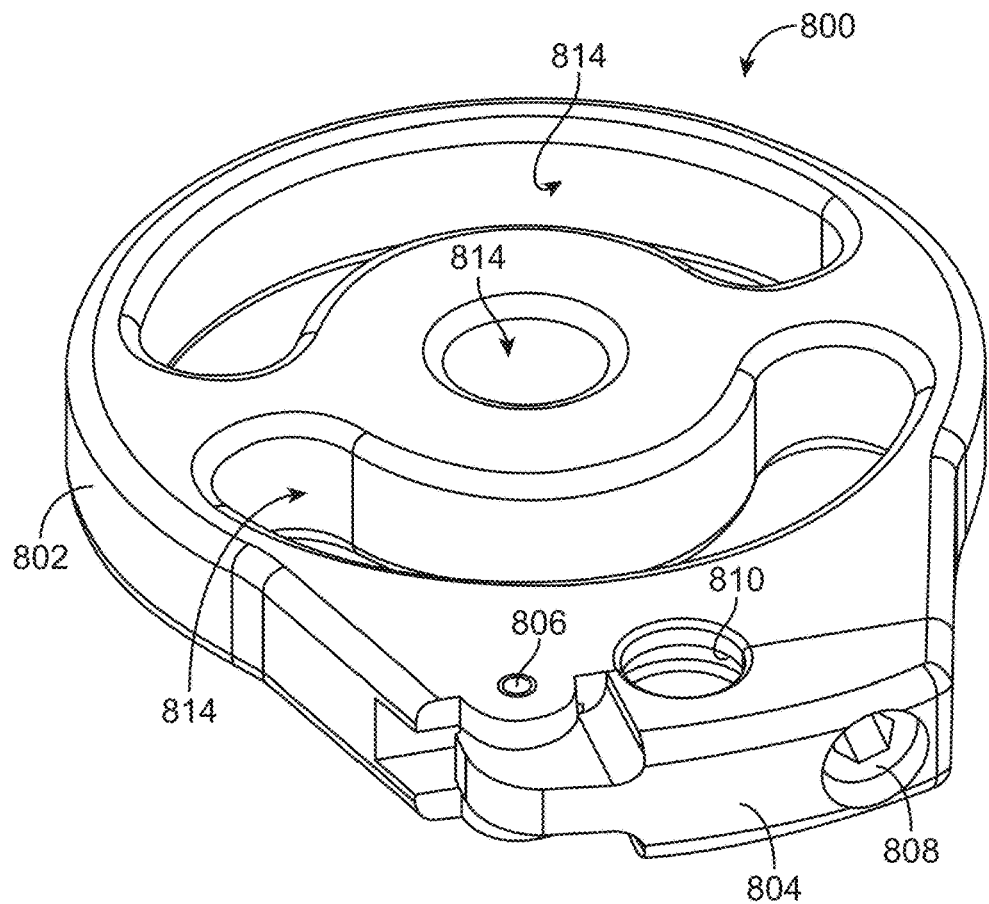
FIG. 13 is a perspective view of one embodiment of a driveline capture portion comprising a circular body of a bone anchor.

With reference now to FIGS. 12 and 13, perspective view of embodiments of a driveline capture portion 800 is shown. The driveline capture portion 800 can comprise a variety of shapes and sizes and can be made from a variety of materials. In some embodiments, the bone anchors disclosed herein, and the components of the bone anchors disclosed herein can comprise one or several biocompatible materials.

Similarly, the driveline capture portion 800 can comprise one or several biocompatible materials.

The driveline capture portion 800 can comprise a body 802 and a moveable clamp element 804. The clamp element 804 can be pivotably connected to the body 802 by the pivot 806. The clamp element 804 can be secured to the body 802 in closed position by a securement feature 808 which can be, for example, a screw. Together, the clamp element 804 and the body 802 define an aperture 810 that can be the driveline receiver. As further seen in FIGS. 12 and 13, the aperture 810 can comprise a plurality of features that can secure the position of the driveline 266 with respect to the aperture 810. Specifically, these features that can be the driveline anchor and that can include one or several grooves, ridges, or the like. In some embodiments, the aperture 810 can comprise a diameter that is less than the diameter of the driveline 266 such that the driveline is secured within the aperture when the clamp element 804 is in the closed position.

The driveline capture portion 800 can further include one or several attachment features 814 located in the body 802 of the driveline capture portion 800. In some embodiments, these one or several attachment features 814 can interact with other features of the bone anchor to secure the driveline capture portion 800 with respect to the bone. Embodiments connecting to the driveline capture portion 800 via the attachment features 814 are shown in FIGS. 14 and 15.

Figure 14:
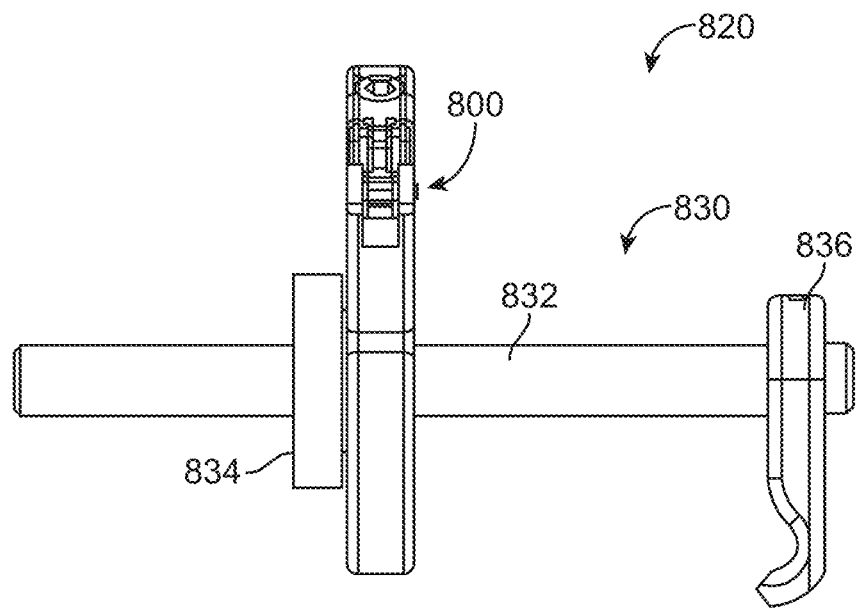
FIG. 14 is a side view of one embodiment of a driveline capture portion connected to a clamp member.
Figure 15:
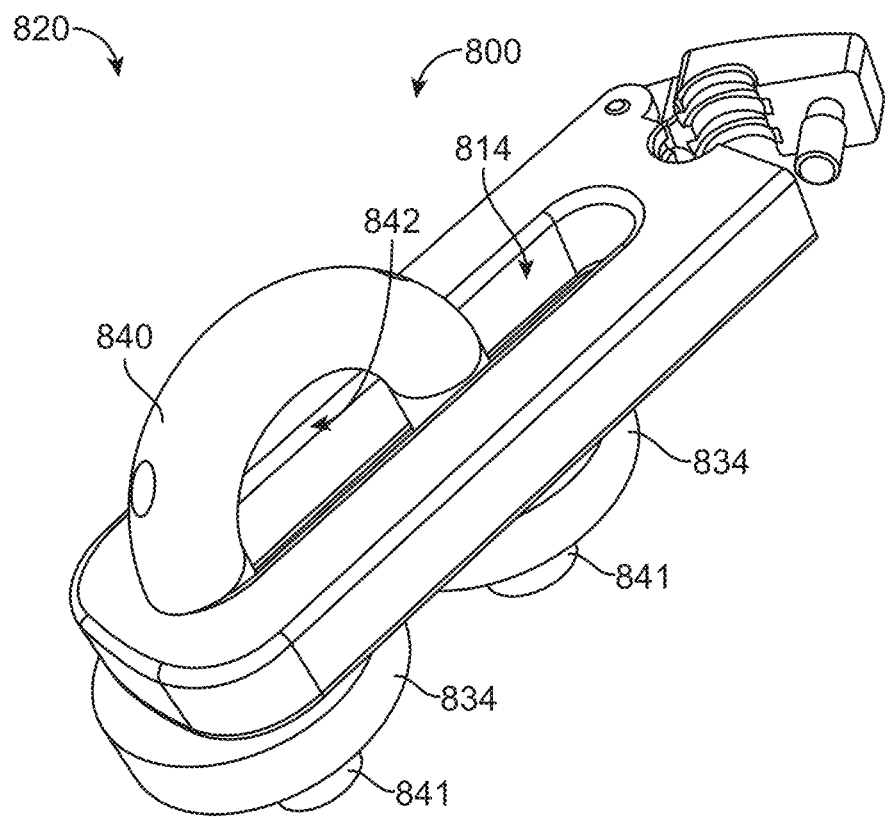
FIG. 15 is a perspective view of one embodiment of a driveline capture portion comprising an elongate body coupled with a U-bolt.
Figure 16:
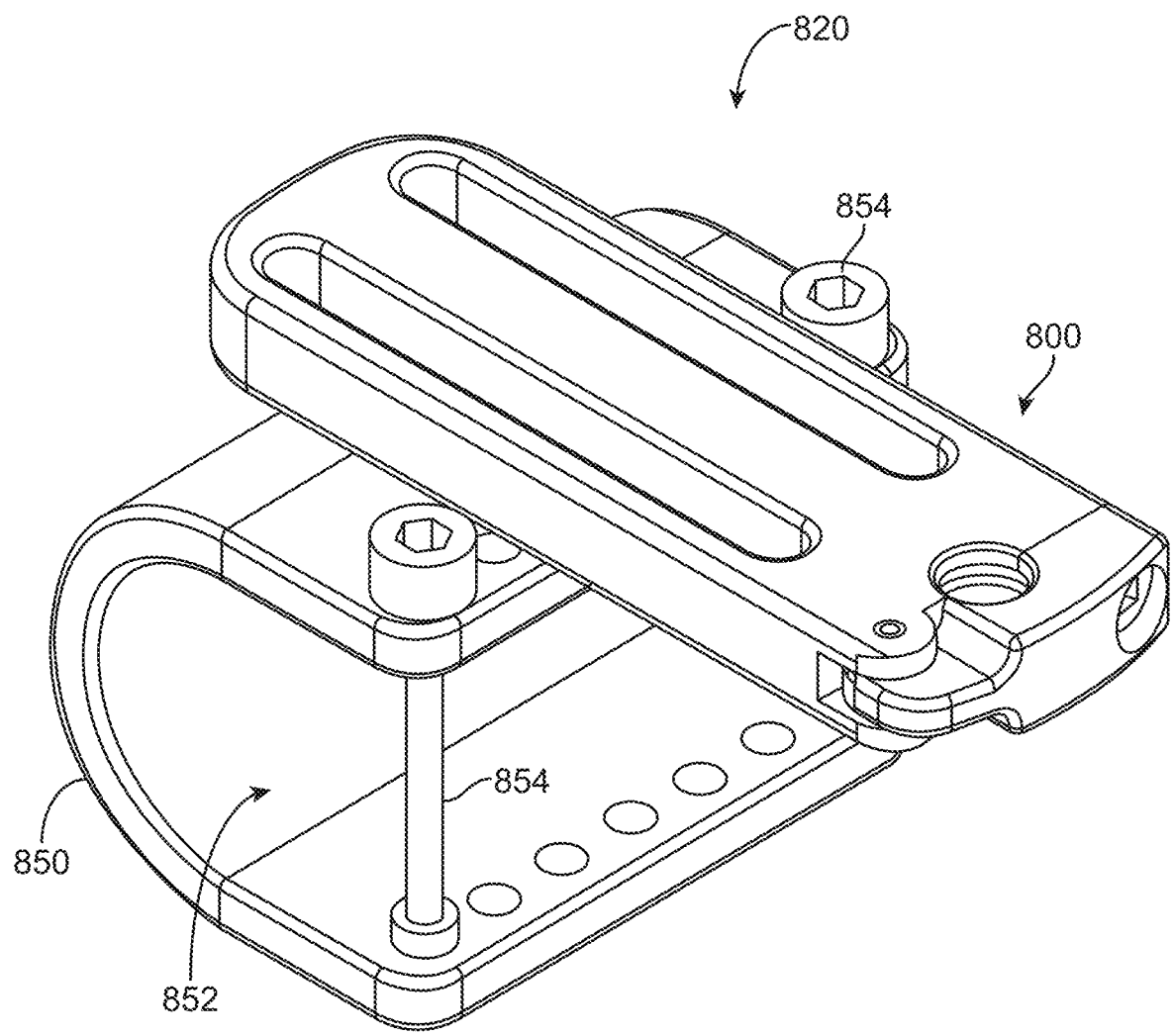
FIG. 16 is a perspective view of one embodiment of a driveline capture portion comprising an elongate body coupled to a U-channel.

With reference to FIGS. 14 through 16 embodiments of a bone anchor 820 are shown. As seen in FIG. 14, a bone anchor 820 can include the driveline capture portion 800 connected to a clamping portion 836 via a shaft 832 and an adjustment feature 834. In some embodiments, the shaft 832 can comprise a cylindrical, elongate member that can extend through at least one of the one or several attachment features 814. In some embodiments, the shaft 832 can comprise a threaded shaft. The shaft 832 can be attached to an adjustment feature 834 that can be, for example, a nut, a thumb-screw, or other mechanical features as would be understood by one of skill from the description herein. In some embodiments, the tightening of the adjustment feature 834 can result in the displacement of the clamping portion 836 relatively towards the driveline capture portion 800. In some embodiments, the adjustment feature 834 can be tightened such that the bone is clamped between the driveline capture portion 800 and the clamping member 836. In such an embodiment, one or both of the driveline capture portion 800 and the clamping member 836 can comprise the bone capture portion 280.

As seen in FIG. 15 the bone anchor 820 can include the driveline capture portion 800 receiving a U-shaped member, and specifically a U-bolt 840, in its one or several attachment features 814. The U-bolt 840 can include ends 841, one or both of which can be connected to an adjustment feature 834 that can change the size of a receiving volume 842 defined by the U-bolt 840 and the driveline capture portion 800 by the tightening or loosening of one or both of the adjustment features 834. In some embodiments, the U-bolt 840 and the driveline capture portion 800 together define the bone capture portion 280. The adjustment features 834 can be one or several nuts, thumbscrews, or other mechanical features as would be understood by one of skill from the description herein. In some embodiments of the bone anchor 820 shown in FIG. 15, the U-bolt 840 can be passed around the bone and the ends 841 can be inserted through the one or several attachment features 814 to capture the bone within the receiving volume 842. The adjustment features 834 can be attached to the ends 841 of the U-bolt 840 and can be tightened to a desired tightness and/or torque.

With reference to FIG. 16, a perspective view of the bone anchor 820 is shown. The bone anchor 820 can be attached to a U-shaped member, and specifically to a U-channel 850 that can define a receiving volume 852 for receiving the bone. In some embodiments, the receiving volume 852 can be closed and/or the bone can be secured in the receiving volume 852 by one or several screws 854. In the embodiment of FIG. 16, the U-channel 850 defines the bone capture portion 280.

Figure 17:
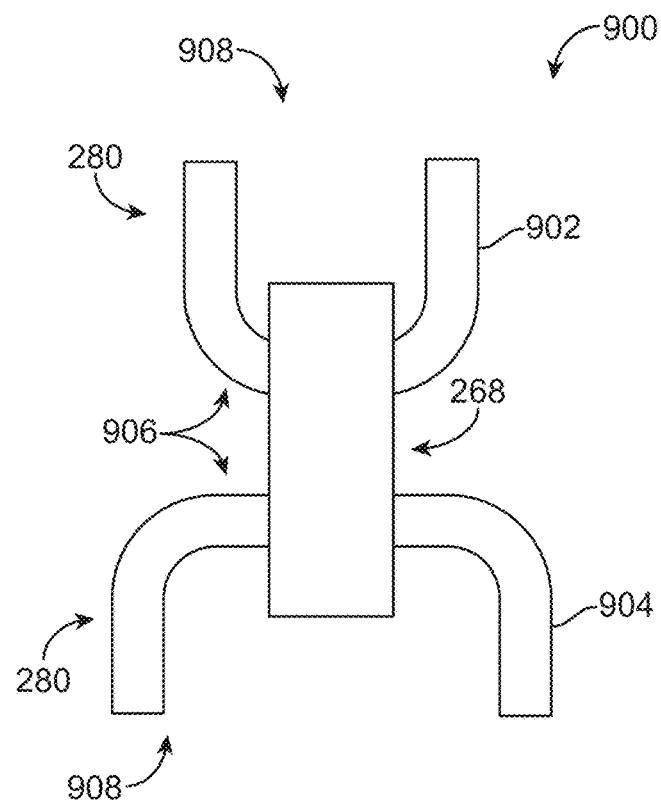
FIG. 17 is a front view of one embodiment of a bone anchor configured for engaging two bones.
Figure 18:
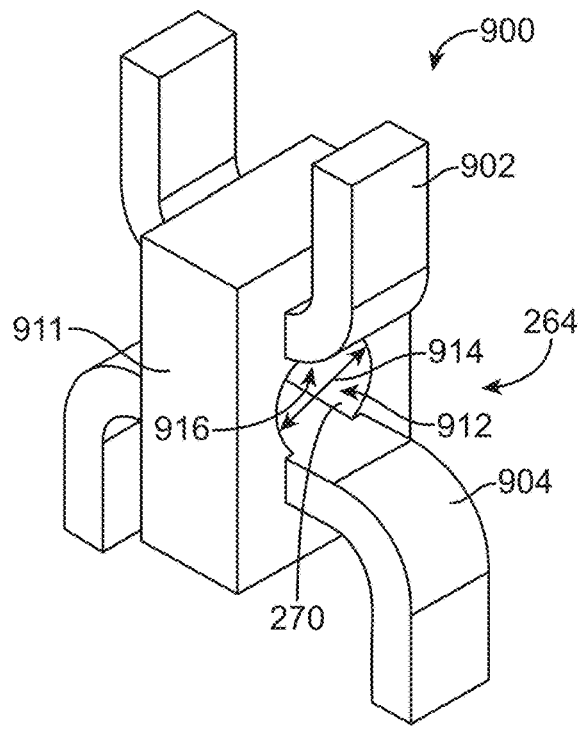
FIG. 18 is a perspective view of one embodiment of a bone anchor configured for engaging two bones.

With reference now to FIGS. 17 and 18 views of an embodiment of a bone anchor 900 are shown. The bone anchor 900 can comprise a variety of sizes and shapes and can be made from a variety of materials. In some embodiments, the bone anchor 900 can comprise one or several features to secure the position of the bone anchor between two bones such as, for example, in the intercostal space between two ribs. As seen in FIG. 17, the bone anchor 900 includes a bone capture portion 280 that comprises a first U-member 902 and a second U-member 904. Each of the U-members 902, 904 comprises a base 906 and a top 908, which is an open top. As seen in FIG. 17, the bases 906 of the U-members 902, 904 are connected, and specifically are connected by the driveline capture portion 264.

The driveline capture portion 264 comprises the driveline receiver 268 and the driveline anchor 270. In the embodiments, the driveline receiver 268 can define a feature such as a channel or aperture that can receive the driveline 266. As specifically shown in FIG. 18, in some embodiments, the driveline receiver 268, which can comprise an elongate member 911 connecting the bases 903 of the U-elements 902, 904, defines an aperture 912 can be, for example, a circular or cylindrical aperture. In some embodiments, the aperture 912 can have a diameter 914. The diameter 914 can be sized with respect to a diameter 276 of the driveline 266 such that the driveline 266 can be received within the aperture 912.

In some embodiments, the diameter 914 of the aperture 912 can be greater than the diameter 276 of the driveline 266, can be equal to the diameter 276 of the driveline 266, or can be less than the diameter 276 of the driveline 266. In some embodiments, the diameter 914 of the aperture 912 can be selected so as to create a friction fit between the driveline 266 and the inner surface 916 of the aperture 912. In some embodiments, this can result in the elastic deformation of all or portions of the driveline receiver 268 and/or the driveline 266 when the driveline 266 is inserted into and/or through the aperture 912.

In some embodiments, the diameter 914 of the aperture 912 can be selected so that an inner surface 916 of the aperture 912, which inner surface 916 can be the driveline anchor 270, engages with the drive line 266 to secure the position of the driveline 266 with respect to the aperture 912. In some embodiments, this inner surface 916 of the aperture 912 can comprise one or several features and/or materials that interact with the driveline 266 to prevent movement of the driveline 266 with respect to the aperture 912. In some embodiments, these one or several features of the inner surface 916 can include, for example, a textured surface, a pitted surface, one or several ribs, one or several grooves, or the like. In some embodiments, these materials can include a high friction material, adhesive, is sticky and/or tacky material, rubber, a deformable material, or the like.

In some embodiments, the driveline 266 can be inserted through the aperture 912 until the bone anchor 900 is at a desired position along the driveline 266. The bone anchor 900 can then be inserted into the intercostal space between two ribs such that one of the ribs is within the first U-member 902 and the other of the ribs is within the second U-member 904, thereby securing the bone anchor 900, and thus the driveline 266 to the ribs.

Figure 19:
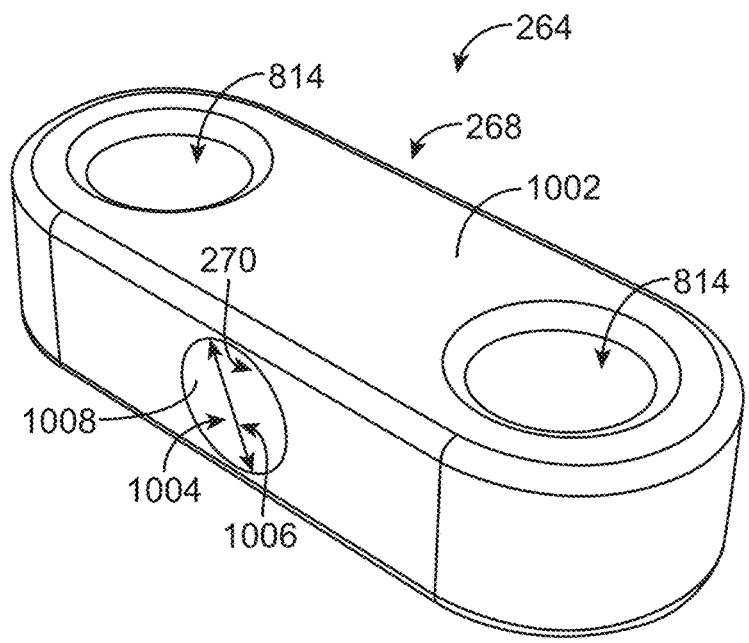
FIG. 19 is a perspective view of one embodiment of a driveline capture portion comprising an elongate body and an aperture.

With reference now to FIG. 19, a perspective view of one embodiment of a driveline capture portion 264 of a bone anchor 1000 is shown. The driveline capture portion 264 comprises the driveline receiver 268 and the driveline anchor 270. In the embodiments, the driveline receiver 268 can define a feature such as a channel or aperture that can receive the driveline 266. As specifically shown in FIG. 19, in some embodiments, the driveline receiver 268, which can comprise an elongate member 1002 defines an aperture 1004 can be, for example, a circular or cylindrical aperture. In some embodiments, the aperture 1004 can have a diameter 1006. The diameter 1006 can be sized with respect to a diameter 276 of the driveline 266 such that the driveline 266 can be received within the aperture 1004.

In some embodiments, the diameter 1006 of the aperture 1004 can be greater than the diameter 276 of the driveline 266, can be equal to the diameter 276 of the driveline 266, or can be less than the diameter 276 of the driveline 266. In some embodiments, the diameter 1006 of the aperture 1004 can be selected so as to create a friction fit between the driveline 266 and the inner surface 1008 of the aperture 1004. In some embodiments, this can result in the elastic deformation of all or portions of the driveline receiver 268 and/or the driveline 266 when the driveline 266 is inserted into and/or through the aperture 1004. In some embodiments, the diameter 1006 of the aperture 1004 can be selected to apply a sufficient force to grip the outer velour and jacket of driveline 266 but not apply a force to the conductors inside the armor layer.

In some embodiments, the diameter 1006 of the aperture 1004 can be selected so that an inner surface 1008 of the aperture 1004, which inner surface 1008 can be the driveline anchor 270, engages with the drive line 266 to secure the position of the driveline 266 with respect to the aperture 1004. In some embodiments, this inner surface 1008 of the aperture 1004 can comprise one or several features and/or materials that interact with the driveline 266 to prevent movement of the driveline 266 with respect to the aperture 1004. In some embodiments, these one or several features of the inner surface 1008 can include, for example, a textured surface, a pitted surface, one or several ribs, or one or several grooves. In some embodiments, these materials can include a high friction material, adhesive, is sticky and/or tacky material, rubber, or a deformable material.

Figure 20:
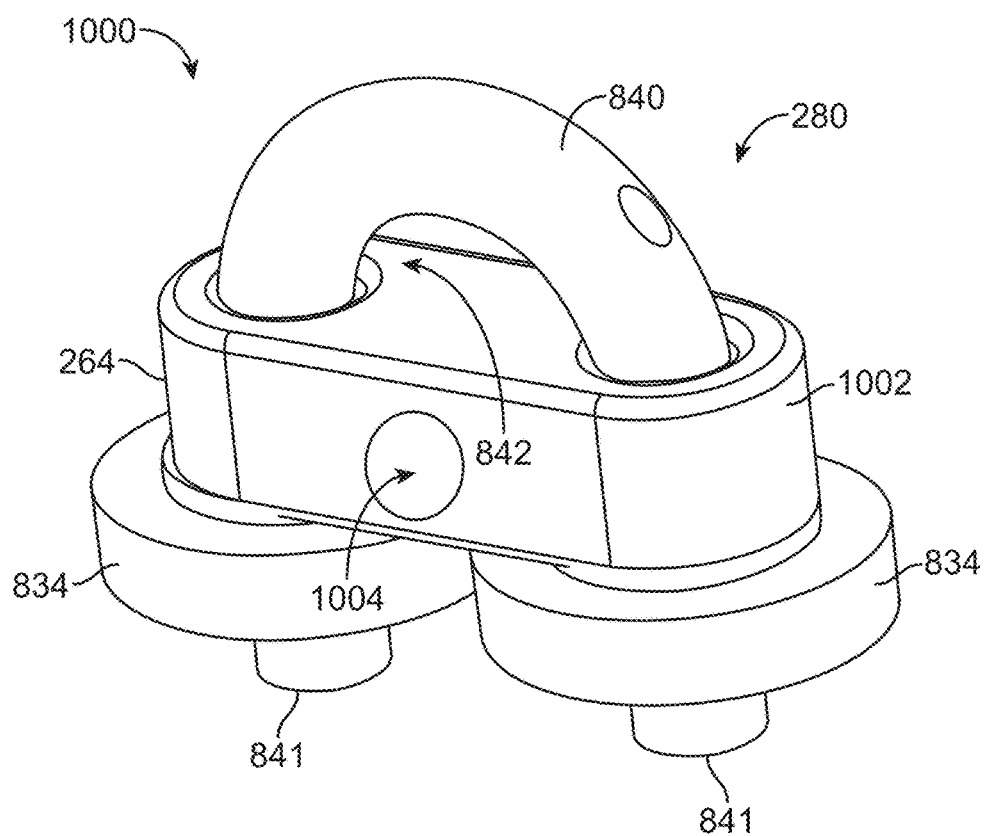
FIG. 20 is a perspective view of one embodiment of a driveline capture portion comprising an elongate body and an aperture coupled with a U-bolt.

As seen in FIG. 20, the driveline capture portion 264 can further include one or several attachment features 814 located in the elongate member 1002 of the driveline capture portion 264. The one or several attachment features 814 can be sized and shape to receive a U-shaped member, and specifically the U-bolt 840, in its one or several attachment features 814. The U-bolt 840 can include ends 841, one or both of which can be connected to an adjustment feature 834 that can change the size of a receiving volume 842 defined by the U-bolt 840 and the driveline capture portion 800 by the tightening or loosening of one or both of the adjustment features 834. In some embodiments, the U-bolt 840 and the driveline capture portion 264 together define the bone capture portion 280. The adjustment features 834 can be one or several nuts, thumbscrews, or other suitable mechanical features as would be understood by one of skill from the description herein. In some embodiments of the bone anchor 820 shown in FIG. 15, the U-bolt 840 can be passed around the bone and the ends 841 can be inserted through the one or several attachment features 814 to capture the bone within the receiving volume 842. The adjustment features 834 can be attached to the ends 841 of the U-bolt 840 and can be tightened to a desired tightness and/or torque.

Figure 21:
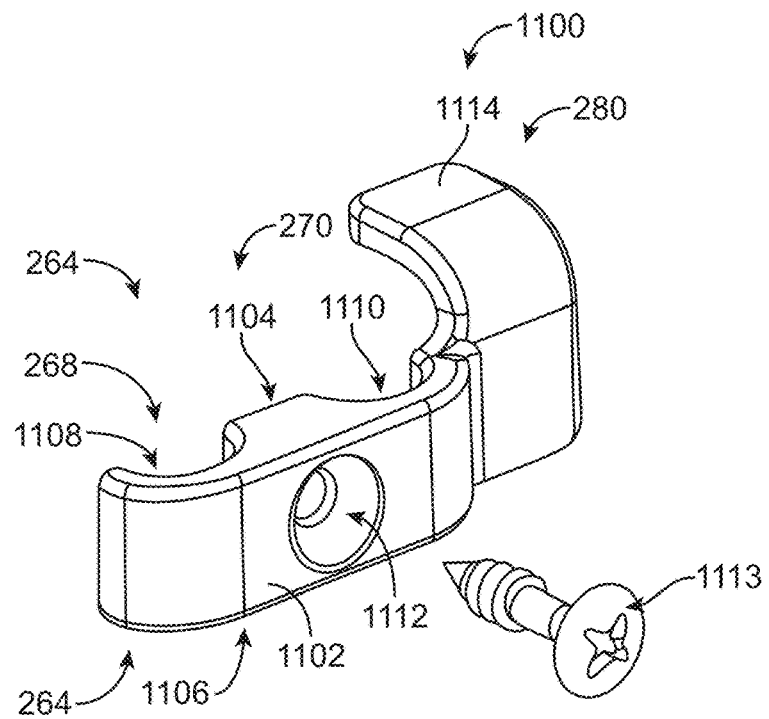
FIG. 21 is a perspective view of one embodiment of a bone anchor comprising a tab.
Figure 22:
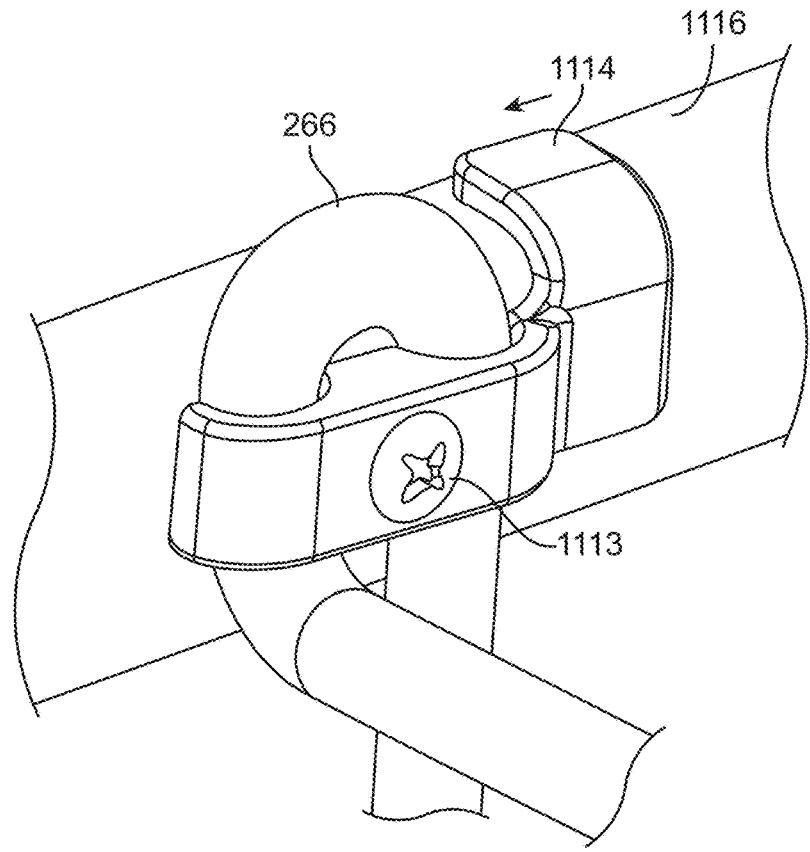
FIG. 22 is a perspective view of one embodiment of a bone anchor comprising a tab coupled to a bone.

FIGS. 21 and 22 show perspective view of one embodiment of a bone anchor 1100. The bone anchor 1100 includes the driveline capture portion 264 including a driveline receiver 268 and a driveline anchor 270. Specifically, the bone anchor 1100 comprises an elongate body 1102 having a back 1104 and a front 1106. The elongate body 1102 is shaped to define a first channel 1108 and a second channel 1110 in the back 1104 of the elongate body, and a screw hole 1112 extending through the elongate body. A screw 1113, which can be a self-tapping screw and/or a captive screw, can be inserted into a bone through the screw hole 1112 to secure the bone anchor 1100 to the bone. The elongate body further includes a bone capture portion 280 in the form of a tab 1114 extending backwardly away from the back 1104 of the elongate body.

In use, and as seen in FIG. 22, the driveline 266 is inserted through the first channel 1108 and the second channel 1110, and the bone anchor is positioned with respect to a bone 1116 such that the tab 1114 engages with a portion of the bone 1116 when the bone anchor 1100 is attached to the bone 1116 via the screw 1113. In some embodiments, the tab 1114 can prevent rotation of the bone anchor 1100 when a torque is applied to the screw 1113 to secure the bone anchor 1100 to the bone. In some embodiments, as the bone anchor 1100 is secured against the bone 1116, a compressive force can be applied to the driveline 266 by the first and second channels 1108, 1110, which can secure and/or set the position of the driveline 266 with respect to the bone anchor 1100. Thus, in some embodiments, the elongate body 1102 and the first and second channels 1108, 1110 are both the driveline receiver 268 and the driveline anchor 270.

Figure 23:
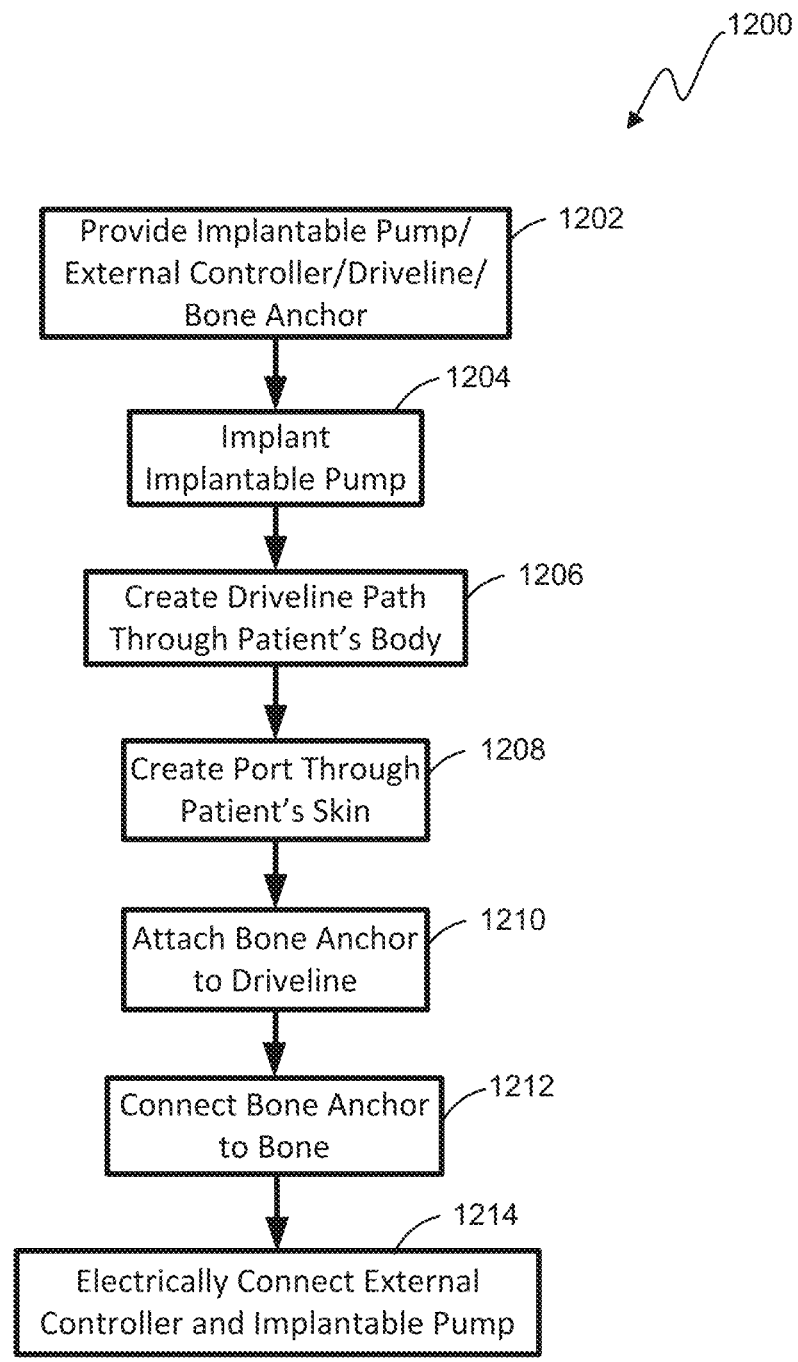
FIG. 23 is a flowchart illustrating one embodiment of a process for affixing a driveline to a bone.

With reference now to FIG. 23, a flowchart illustrating one embodiment of a process 1220 for affixing a driveline to a bone is shown. In some embodiments, this process can be performed, for example, using any of the herein disclosed bone anchors. The process 1200 begins at block 1202, wherein the implantable blood pump 14, the external controller 20, the driveline 26, and the bone anchor are provided. The process 1200 then proceeds to block 1204, wherein the implantable blood pump 14 is implanted. In some embodiments, this can include, for example, connecting the implantable blood pump 14 to desired tissue and/or to one or several desired organs.

At block 1206, a driveline path through the patient's body is created. In some embodiments, this can include the routing of the driveline 26 through the patient's body such that the driveline 26 exits the patient's body at a desired location and/or passes one or several desired bones such as, for example, one or several ribs. At bock 1208, a defect (or driveline exit site) is created through the patient's skin. In some embodiments, this can include the incising of the patient's skin and/or tissue to create a port and/or partially closing a pre-existing incision to create the port. In some embodiments, the defect is created by tunneling or coring a hole in the skin. In some embodiments, and as part of creating the defect, the driveline 26 can be passed through the skin such that a portion of the driveline 26 is inside of the patient's body and another portion of the driveline is outside of the patient's body.

At block 1210, the bone anchor is attached to the driveline 26. In some embodiments, this can include receiving the driveline in the driveline capture portion 264 of the driveline 26 and fixing the position of the driveline 26 with respect to the driveline capture portion 264. This can specifically include receiving the driveline with the driveline receiver 268 of the bone anchor and engaging the driveline 26 with the driveline anchor 270 to fix the position of the driveline 26 with respect to the driveline receiver 268. In some embodiments, this can include inserting the driveline 26 through an aperture of the bone anchor, inserting the driveline through one or several capture hooks, securing the driveline 26 to the bone anchor via a cable tie, securing the driveline 26 to the bone anchor via the attachment of a plate to the driveline receiver 264 and/or by attaching the bone anchor to the bone, securing the driveline 26 to the bone anchor by closing the clamp element 804.

At block 1212, the bone anchor is connected to the bone. In some embodiments, this can include engaging the bone with the bone capture portion 280 of the bone anchor and fixing the position of the bone with respect to the bone anchor and/or any parts of the bone anchor such as the bone capture portion 280 of the bone anchor. In some embodiments, this can include moving bone capture portion 280 to receive the bone within the bone capture portion 280, securing the bone capture portion to the bone via one or several screws, clamps, nails, or other mechanical features, securing the bone capture portion between two bones, e.g., in the intercostal space between two ribs.

At block 1214, the external controller 20 is electrically connected to the implantable pump 14 via the driveline 26. In some embodiments, this can include the providing of power to the implantable pump 14 via the driveline 26 and/or the providing of control signals to the implantable pump 14 via the driveline.

In the preceding description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A bone anchor for securing a driveline to a bone, the driveline connecting an external controller or power source to an implantable blood pump, the bone anchor comprising:
   a driveline capture portion configured to receive the driveline and fix a position of the driveline with respect to the driveline capture portion, wherein the driveline capture portion comprises:
      a driveline receiver configured to receive the driveline, wherein the driveline receiver comprises a channel sized with respect to a diameter of the driveline to permit the driveline to extend through the channel; and
      a driveline anchor configured to engage the driveline to fix the position of the driveline with respect to the driveline receiver; and
   a bone capture portion configured to engage a bone and fix a position of the bone capture portion with respect to the bone.

2. The bone anchor of claim 1, wherein the channel has a diameter less than a diameter of the driveline, and wherein the bone anchor comprises a top, a bottom, a first end, and a second end.

3. The bone anchor of claim 1, wherein the channel of the driveline receiver is configured to cause the driveline to extend through the channel along an axis that is parallel to a plane formed by the bone capture portion.

4. The bone anchor of claim 1, wherein the channel is cylindrical or circular, and wherein the driveline is retained within the channel by a friction fit.

5. A system for securing a driveline to a bone via a bone anchor, the driveline electrically connecting an external controller and an implantable blood pump, the system comprising:
   an implantable blood pump comprising a rotor and a stator;
   an external controller configured to power the implantable blood pump and provide a control signal to the implantable blood pump;

a percutaneous driveline electrically connecting the implantable blood pump and the external controller, wherein the percutaneous driveline has a diameter; and a bone anchor comprising:
- a driveline capture portion configured to receive the driveline and fix a position of the driveline with respect to the driveline capture portion, wherein the driveline capture portion comprises a channel sized with respect to a diameter of the driveline to permit the driveline to extend through the channel; and
- a bone capture portion configured to receive a bone and fix a position of the bone capture portion with respect to the bone.

6. The system of claim 5, wherein the channel having a diameter less than the diameter of the percutaneous driveline.

7. A method for affixing a driveline to a bone, wherein the driveline electrically connects an external controller to an implantable blood pump, the method comprising:
- implanting the implantable blood pump in a patient's body;
- creating a driveline path through a patient's body, wherein the driveline passes at least one bone;
- connecting the driveline to a bone anchor via a driveline capture portion configured to receive the driveline and fix a position of the driveline with respect to the driveline capture portion, wherein the driveline capture portion comprises:
  - a driveline receiver configured to receive the driveline, wherein the driveline receiver comprises a channel sized with respect to a diameter of the driveline to permit the driveline to extend through the channel; and
  - a driveline anchor configured to engage the driveline to fix the position of the driveline with respect to the driveline receiver;
- connecting the bone anchor to the at least one bone via a bone capture portion configured to engage a bone and fix a position of the bone capture portion with respect to the bone; and
- electrically connecting the external controller and the implantable blood pump.

8. The method of claim 7, wherein connecting the driveline to the bone anchor via the driveline capture portion comprises receiving the driveline in the driveline receiver and fixing the position of the driveline with respect to the driveline receiver via the driveline anchor.

9. The method of claim 8, wherein the channel comprises a diameter less than a diameter of the driveline.

10. The method of claim 8, wherein the bone anchor comprises a top, a bottom, a first end, and a second end, and wherein the driveline anchor comprises a plurality of capture hooks.

11. The method of claim 10, wherein fixing the position of the driveline with respect to the driveline receiver via the driveline anchor comprises inserting the driveline through the plurality of capture hooks, wherein each of the plurality of capture hooks extend towards the top of the bone anchor and are spaced between the first and second ends of the bone anchor.

12. The method of claim 11, wherein at least some of the capture hooks, together with the driveline receiver define a first channel configured to hold the driveline in a first orientation, and wherein at least one of the capture hooks, together with the driveline receiver defines a second channel configured to hold the driveline in a second orientation.

13. The method of claim 12, wherein the driveline in the first orientation is perpendicular to the driveline in the second orientation.

14. The method of claim 7, wherein electrically connecting the external controller and the implantable blood pump comprises providing at least one of: power; or a control signal to the implantable blood pump via the driveline.

* * * * *